•

US010329358B2

(12) United States Patent
Miyakoshi et al.

(10) Patent No.: US 10,329,358 B2
(45) Date of Patent: Jun. 25, 2019

(54) ANTI-HUMAN MEMBRANE-TYPE ADAM28 ANTIBODY

(71) Applicants: GeneFrontier Corporation, Kashiwa-shi, Chiba (JP); KEIO UNIVERSITY, Tokyo (JP)

(72) Inventors: Akira Miyakoshi, Kashiwa (JP); Kanehisa Kojoh, Kashiwa (JP); Satsuki Mochizuki, Tokyo (JP); Masayuki Shimoda, Tokyo (JP); Yasunori Okada, Tokyo (JP)

(73) Assignees: GeneFrontier Corporation, Chiba (JP); KEIO UNIVERSITY, Tokyo (JP)

( * ) Notice: Subject to any disclaimer, the term of this patent is extended or adjusted under 35 U.S.C. 154(b) by 0 days.

(21) Appl. No.: 15/556,177

(22) PCT Filed: Mar. 4, 2016

(86) PCT No.: PCT/JP2016/056810
§ 371 (c)(1),
(2) Date: Sep. 6, 2017

(87) PCT Pub. No.: WO2016/143702
PCT Pub. Date: Sep. 15, 2016

(65) Prior Publication Data
US 2018/0044435 A1 Feb. 15, 2018

(30) Foreign Application Priority Data
Mar. 6, 2015 (JP) ................................. 2015-045244

(51) Int. Cl.
C07K 16/00 (2006.01)
C07K 16/40 (2006.01)
C07K 16/30 (2006.01)
A61K 47/68 (2017.01)
C07K 16/28 (2006.01)

(52) U.S. Cl.
CPC .......... C07K 16/40 (2013.01); A61K 47/6871 (2017.08); C07K 16/2896 (2013.01); C07K 16/30 (2013.01); C07K 2317/33 (2013.01); C07K 2317/34 (2013.01); C07K 2317/56 (2013.01); C07K 2317/565 (2013.01)

(58) Field of Classification Search
None
See application file for complete search history.

(56) References Cited

U.S. PATENT DOCUMENTS 5,530,101 A    6/1996  Queen et al.
5,693,762 A *  12/1997 Queen .................... C07K 16/00
                                                    424/133.1
9,845,364 B2   12/2017 Miyakoshi et al.
2009/0053213 A1  2/2009  Steidl et al.
2009/0252733 A1 10/2009  Tesar
2015/0274840 A1 10/2015  Miyakoshi et al.

FOREIGN PATENT DOCUMENTS

CN       101218255 A      7/2008
CN       101287764 A     10/2008
WO   WO 2014/073292 A1    5/2015

OTHER PUBLICATIONS

Rudikoff et al. (Proceedings of the National Academy of Sciences, 1982, 79:1979-1983).*
Mitsui et al (Cancer Research, 2006, 66(20): 9913-9920).*
U.S. Appl. No. 14/440,391, filed May 4, 2015.
Abe et al., "ADAM28 expression in oncogene-transformed cells and human carcinoma cells," XXIIIrd FECTS and ISMB Joint Meeting, Abstract P5.1 (Aug. 2012).
Abe et al., "Src Plays a Key Role in ADAM28 Expression in v-src—Transformed Epithelial Cells and Human Carcinoma Cells," Am. J. Pathol., 183(5): 1667-1678 (2013).
Bridges et al., "The Lymphocyte Metalloprotease MDC-L (ADAM 28) Is a Ligand for the Integrin $\alpha_4\beta_1$," J. Biol. Chem., 277(5): 3784-3792 (2002).
Bridges et al., "Integrin $\alpha 4\beta 1$-Dependent Adhesion to ADAM 28 (MDC-L) Requires an Extended Surface of the Disintegrin Domain," Biochemistry, 42(13): 3734-3741 (2003).
Bridges et al., "ADAM disintegrin-like domain recognition by the lymphocyte integrins $\alpha 4\beta 1$ and $\alpha 4\beta 7$," Biochem. J., 387: 101-108 (2005).
Brown et al., "Tolerance of a single, but not multiple, amino acid replacements in antibody VH CDR 2: a means of minimizing B cell wastage from somatic hypermutation?" J. Immunol., 156(9): 3285-3291 (1996).
Fourie et al., "Catalytic Activity of ADAM8, ADAM15, and MDC-L (ADAM28) on Synthetic Peptide Substrates and in Ectodomain Cleavage of CD23," J. Biol. Chem., 278(33): 30469-30477 (2003).
Hikichi et al., "All-trans retinoic acid-induced ADAM28 degrades proteoglycans in human chondrocytes," Biochem. Biophys. Res. Commun., 386(2): 294-299 (2009).
Howard et al., "Cloning and characterization of ADAM28: evidence for autocatalytic pro-domain removal and for cell surface localization of mature ADAM28," Biochem. J., 348: 21-27 (2000).
Kuroda et al., "ADAM28 is a serological and histochemical marker for non-small-cell lung cancers," Int. J. Cancer, 127(8): 1844-1856 (2010).
Mitsui et al., "ADAM28 Is Overexpressed in Human Breast Carcinomas: Implications for Carcinoma Cell Proliferation through Cleavage of Insulin-like Growth Factor Binding Protein-3," Cancer Res., 66(20): 9913-9920 (2006).
Mochizuki et al., "ADAM28 is activated by MMP-7 (matrilysin-1) and cleaves insulin-like growth factor binding protein-3," Biochem. Biophys. Res. Commun., 315(1): 79-84 (2004).

(Continued)

Primary Examiner — Sean E Aeder
(74) Attorney, Agent, or Firm — Osha Liang LLP

(57) ABSTRACT

The present invention provides an antibody having an activity to specifically bind to human membrane-anchored form ADAM28 at an epitope in a region of the 524th-659th amino acids in the amino acid sequence shown in SEQ ID NO: 2. In addition, the present invention provides a drug delivery vehicle for delivering a drug to a cell or tissue that expresses human membrane-anchored form ADAM28, which contains the antibody.

14 Claims, 4 Drawing Sheets
Specification includes a Sequence Listing.

(56) References Cited

OTHER PUBLICATIONS

Mochizuki et al., "ADAMs in cancer cell proliferation and progression," *Cancer Sci.*, 98(5): 621-628 (2007).
Mochizuki et al., "Connective tissue growth factor is a substrate of ADAM28," *Biochem. Biophys. Res. Commun.*, 402(4): 651-657 (2010).
Mochizuki et al., "Effect of ADAM28 on Carcinoma Cell Metastasis by Cleavage of von Willebrand Factor," *J. Natl. Cancer Inst.*, 104(12): 906-922 (2012).
Mochizuki et al., "Effects of human antibodies against ADAM28 on cancer cell growth and metastasis," *The Dutch Society for Matrix Biology (NVMB), the Netherlands Institute for Regenerative Medicine (NIRM), and the International Society for Matrix Biology (ISMB)—1$^{st}$ MBE (Matrix Biology Europe) Conference*, p. 152, Abstract 116 (Jun. 2014).
Ohtsuka et al., "ADAM28 is overexpressed in human non-small cell lung carcinomas and correlates with cell proliferation and lymph node metastasis," *Int. J. Cancer*, 118(2): 263-273 (2006).
Okada et al., "Growth, infiltration, and metastasis of cancer cells via micro-environmental factor metabolism in cancer cells by means of MMP and ADAM: ADAM28 gene expression, development of human anti-ADAM28 antibody, and cancer cell growth and metastasis suppression," Ministry of Health, Labor and Science Research Grant on Third Comprehensive Anti-Cancer Strategy Research Projects, Research Contributing to Analyses of Pathology and Pathological Molecular Basis of Important Clinical Characteristics of Cancer, Research Synthesis Report, pp. 9-12 (2014).
Roemer et al., "Increased mRNA expression of ADAMs in renal cell carcinoma and their association with clinical outcome," *Oncol. Rep.*, 11(2): 529-536 (2004).
Roemer et al., "The Membrane Proteases ADAMs and Hepsin are Differentially Expressed in Renal Cell Carcinoma. Are They Potential Tumor Markers?" *J. Urol.*, 172(6): 2162-2166 (2004).
Rothe et al., "The Human Combinatorial Antibody Library HuCAL GOLD Combines Diversification of All Six CDRs According to the Natural Immune System with a Novel Display Method for Efficient Selection of High-Affinity Antibodies," *J. Mol. Biol.*, 376(4): 1182-1200 (2008).
Shimoda et al., "Binding of ADAM28 to P-selectin Glycoprotein Ligand-1 Enhances P-selectin-mediated Leukocyte Adhesion to Endothelial Cells," *J. Biol. Chem.*, 282(35): 25864-25874 (2007).
Takeda et al., "Crystal structures of VAP1 reveal ADAMs' MDC domain architecture and its unique C-shaped scaffold," *EMBO J.*, 25(11): 2388-2396 (2006).
UniProt, "Disintegrin and metalloproteinase domain-containing protein 28 (ADAM28)," UniProtKB Accession No. Q9UKQ2 (ADA28_HUMAN) (published Jun. 20, 2001).
Vajdos et al., "Comprehensive Functional Maps of the Antigen-binding Site of an Anti-ErbB2 Antibody Obtained with Shotgun Scanning Mutagenesis," *J. Mol. Biol.*, 320(2): 415-428 (2002).
Zucker et al., "New Wrinkle Between Cancer and Blood Coagulation: Metastasis and Cleavage of von Willebrand Factor by ADAM28," *J. Natl. Cancer Inst.*, 104(12): 887-888 (2012).
Japanese Patent Office, International Search Report in International Patent Application No. PCT/JP2013/076745 (dated Dec. 3, 2013).
Japanese Patent Office, International Search Report in International Patent Application No. PCT/JP2016/056810 (dated May 24, 2016).
Japanese Patent Office, Written Opinion of the International Searching Authority in International Patent Application No. PCT/JP2016/056810 (dated May 24, 2016).

\* cited by examiner

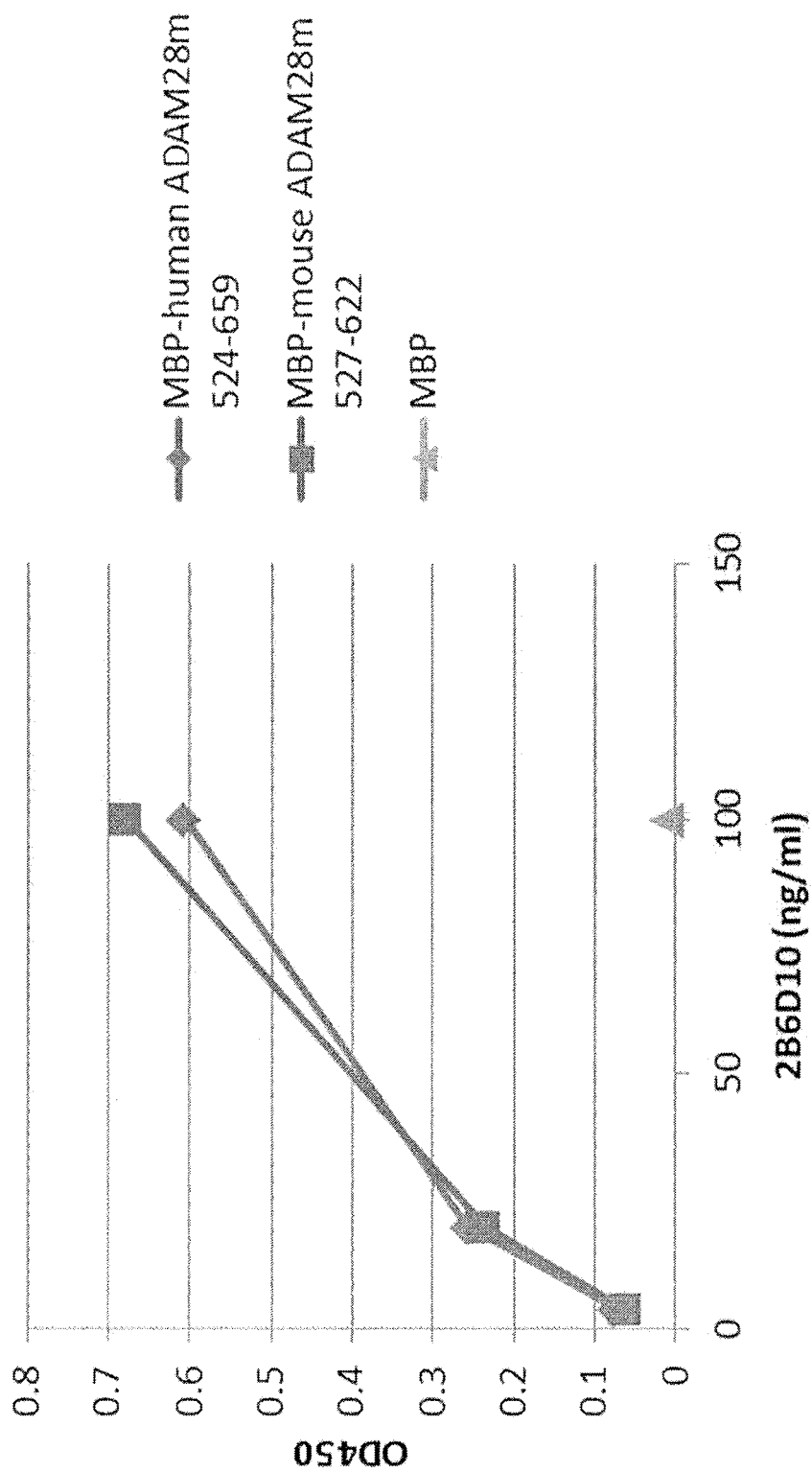

SEQUENCE LISTING

```
<160> NUMBER OF SEQ ID NOS: 27

<210> SEQ ID NO 1
<211> LENGTH: 2328
<212> TYPE: DNA
<213> ORGANISM: Homo sapiens
<220> FEATURE:
<221> NAME/KEY: CDS
<222> LOCATION: (1)..(2328)

<400> SEQUENCE: 1 atg ttg caa ggt ctc ctg cca gtc agt ctc ctc ctc tct gtt gca gta      48
Met Leu Gln Gly Leu Leu Pro Val Ser Leu Leu Leu Ser Val Ala Val
1               5                   10                  15 agt gct ata aaa gaa ctc cct ggg gtg aag aag tat gaa gtg gtt tat      96
Ser Ala Ile Lys Glu Leu Pro Gly Val Lys Lys Tyr Glu Val Val Tyr
            20                  25                  30 cct ata aga ctt cat cca ctg cat aaa aga gag gcc aaa gag cca gag     144
Pro Ile Arg Leu His Pro Leu His Lys Arg Glu Ala Lys Glu Pro Glu
        35                  40                  45 caa cag gaa caa ttt gaa act gaa tta aag tat aaa atg aca att aat     192
Gln Gln Glu Gln Phe Glu Thr Glu Leu Lys Tyr Lys Met Thr Ile Asn
    50                  55                  60 gga aaa att gca gtg ctt tat ttg aaa aaa aac aag aac ctc ctt gca     240
Gly Lys Ile Ala Val Leu Tyr Leu Lys Lys Asn Lys Asn Leu Leu Ala
65                  70                  75                  80 cca ggc tac acg gaa aca tat tat aat tcc act gga aag gag atc acc     288
Pro Gly Tyr Thr Glu Thr Tyr Tyr Asn Ser Thr Gly Lys Glu Ile Thr
                85                  90                  95 aca agc cca caa att atg gat gat tgt tat tat caa gga cat att ctt     336
```

```
                    Thr Ser Pro Gln Ile Met Asp Asp Cys Tyr Tyr Gln Gly His Ile Leu
                                100                 105                 110 aat gaa aag gtt tct gac gct agc atc agc aca tgt agg ggt cta agg           384
Asn Glu Lys Val Ser Asp Ala Ser Ile Ser Thr Cys Arg Gly Leu Arg
        115                 120                 125 ggc tac ttc agt cag ggg gat caa aga tac ttt att gaa cct tta agc           432
Gly Tyr Phe Ser Gln Gly Asp Gln Arg Tyr Phe Ile Glu Pro Leu Ser
    130                 135                 140 ccc ata cat cgg gat gga cag gag cat gca ctc ttc aag tat aac cct           480
Pro Ile His Arg Asp Gly Gln Glu His Ala Leu Phe Lys Tyr Asn Pro
145                 150                 155                 160 gat gaa aag aat tat gac agc acc tgt ggg atg gat ggt gtg ttg tgg           528
Asp Glu Lys Asn Tyr Asp Ser Thr Cys Gly Met Asp Gly Val Leu Trp
                165                 170                 175 gcc cac gat ttg cag cag aac att gcc cta cct gcc acc aaa cta gta           576
Ala His Asp Leu Gln Gln Asn Ile Ala Leu Pro Ala Thr Lys Leu Val
            180                 185                 190 aaa ttg aaa gac agg aag gtt cag gaa cat gag aaa tac ata gaa tat           624
Lys Leu Lys Asp Arg Lys Val Gln Glu His Glu Lys Tyr Ile Glu Tyr
        195                 200                 205 tat ttg gtc ctg gat aat ggt gag ttt aaa agg tac aat gag aat caa           672
Tyr Leu Val Leu Asp Asn Gly Glu Phe Lys Arg Tyr Asn Glu Asn Gln
    210                 215                 220 gat gag atc aga aag agg gta ttt gag atg gct aat tat gtc aac atg           720
Asp Glu Ile Arg Lys Arg Val Phe Glu Met Ala Asn Tyr Val Asn Met
225                 230                 235                 240 ctt tat aaa aag ctc aat act cat gtg gcc tta gtt ggt atg gaa atc           768
Leu Tyr Lys Lys Leu Asn Thr His Val Ala Leu Val Gly Met Glu Ile
                245                 250                 255 tgg act gac aag gat aag ata aag ata acc cca aat gca agc ttc acc           816
Trp Thr Asp Lys Asp Lys Ile Lys Ile Thr Pro Asn Ala Ser Phe Thr
            260                 265                 270 ttg gag aat ttt tct aaa tgg agg ggg agt gtt ctc tca aga aga aag           864
Leu Glu Asn Phe Ser Lys Trp Arg Gly Ser Val Leu Ser Arg Arg Lys
        275                 280                 285 cgt cat gat att gct cag tta atc aca gca aca gaa ctt gct gga acg           912
Arg His Asp Ile Ala Gln Leu Ile Thr Ala Thr Glu Leu Ala Gly Thr
    290                 295                 300 act gtg ggt ctt gca ttt atg tct aca atg tgt tct cct tat tct gtt           960
Thr Val Gly Leu Ala Phe Met Ser Thr Met Cys Ser Pro Tyr Ser Val
305                 310                 315                 320 ggc gtt gtt cag gac cac agc gat aat ctt ctt aga gtt gca ggg aca          1008
Gly Val Val Gln Asp His Ser Asp Asn Leu Leu Arg Val Ala Gly Thr
                325                 330                 335 atg gca cat gaa atg ggc cac aac ttt gga atg ttt cat gac gac tat          1056
Met Ala His Glu Met Gly His Asn Phe Gly Met Phe His Asp Asp Tyr
            340                 345                 350 tct tgc aag tgt cct tct aca ata tgt gtg atg gac aaa gca ctg agc          1104
Ser Cys Lys Cys Pro Ser Thr Ile Cys Val Met Asp Lys Ala Leu Ser
        355                 360                 365 ttc tat ata ccc aca gac ttc agt tcc tgc agc cgt ctc agc tat gac          1152
Phe Tyr Ile Pro Thr Asp Phe Ser Ser Cys Ser Arg Leu Ser Tyr Asp
    370                 375                 380 aag ttt ttt gaa gat aaa tta tca aat tgc ctc ttt aat gct cca ttg          1200
Lys Phe Phe Glu Asp Lys Leu Ser Asn Cys Leu Phe Asn Ala Pro Leu
385                 390                 395                 400 cct aca gat atc ata tcc act cca att tgt ggg aac cag ttg gtg gaa          1248
Pro Thr Asp Ile Ile Ser Thr Pro Ile Cys Gly Asn Gln Leu Val Glu
                405                 410                 415
```

```
atg gga gag gac tgt gat tgt ggg aca tct gag gaa tgt acc aat att    1296
Met Gly Glu Asp Cys Asp Cys Gly Thr Ser Glu Glu Cys Thr Asn Ile
                420             425             430 tgc tgt gat gct aag aca tgt aaa atc aaa gca act ttt caa tgt gca    1344
Cys Cys Asp Ala Lys Thr Cys Lys Ile Lys Ala Thr Phe Gln Cys Ala
            435             440             445 tta gga gaa tgt tgt gaa aaa tgc caa ttt aaa aag gct ggg atg gtg    1392
Leu Gly Glu Cys Cys Glu Lys Cys Gln Phe Lys Lys Ala Gly Met Val
        450             455             460 tgc aga cca gca aaa gat gag tgc gac ctg cct gaa atg tgt aat ggt    1440
Cys Arg Pro Ala Lys Asp Glu Cys Asp Leu Pro Glu Met Cys Asn Gly
465             470             475             480 aaa tct ggt aat tgt cct gat gat aga ttc caa gtc aat ggc ttc cct    1488
Lys Ser Gly Asn Cys Pro Asp Asp Arg Phe Gln Val Asn Gly Phe Pro
            485             490             495 tgc cat cac ggg aag ggc cac tgc ttg atg ggg aca tgc ccc aca ctg    1536
Cys His His Gly Lys Gly His Cys Leu Met Gly Thr Cys Pro Thr Leu
        500             505             510 cag gag cag tgc aca gag ctg tgg gga cca gga act gag gtt gca gat    1584
Gln Glu Gln Cys Thr Glu Leu Trp Gly Pro Gly Thr Glu Val Ala Asp
            515             520             525 aag tca tgt tac aac agg aat gaa ggt ggg tca aag tac ggg tac tgt    1632
Lys Ser Cys Tyr Asn Arg Asn Glu Gly Gly Ser Lys Tyr Gly Tyr Cys
        530             535             540 cgc aga gtg gat gac aca ctc att ccc tgc aaa gca aat gat acc atg    1680
Arg Arg Val Asp Asp Thr Leu Ile Pro Cys Lys Ala Asn Asp Thr Met
545             550             555             560 tgt ggg aag ttg ttc tgt caa ggt ggg tcg gat aat ttg ccc tgg aaa    1728
Cys Gly Lys Leu Phe Cys Gln Gly Gly Ser Asp Asn Leu Pro Trp Lys
            565             570             575 gga cgg ata gtg act ttc ctg aca tgt aaa aca ttt gat cct gaa gac    1776
Gly Arg Ile Val Thr Phe Leu Thr Cys Lys Thr Phe Asp Pro Glu Asp
        580             585             590 aca agt caa gaa ata ggc atg gtg gcc aat gga act aag tgt ggc gat    1824
Thr Ser Gln Glu Ile Gly Met Val Ala Asn Gly Thr Lys Cys Gly Asp
            595             600             605 aac aag gtt tgc att aat gca gaa tgt gtg gat att gag aaa gcc tac    1872
Asn Lys Val Cys Ile Asn Ala Glu Cys Val Asp Ile Glu Lys Ala Tyr
        610             615             620 aaa tca acc aat tgc tca tct aag tgc aaa gga cat gct gtg tgt gac    1920
Lys Ser Thr Asn Cys Ser Ser Lys Cys Lys Gly His Ala Val Cys Asp
625             630             635             640 cat gag ctc cag tgt caa tgt gag gaa gga tgg atc cct ccc gac tgc    1968
His Glu Leu Gln Cys Gln Cys Glu Glu Gly Trp Ile Pro Pro Asp Cys
            645             650             655 gat gac tcc tca gtg gtc ttc cac ttc tcc att gtg gtt ggg gtg ctg    2016
Asp Asp Ser Ser Val Val Phe His Phe Ser Ile Val Val Gly Val Leu
        660             665             670 ttc cca atg gcg gtc att ttt gtg gtg gtt gct atg gta atc cgg cac    2064
Phe Pro Met Ala Val Ile Phe Val Val Val Ala Met Val Ile Arg His
            675             680             685 cag agc tcc aga gaa aag cag aag aaa gat cag agg cca cta tct acc    2112
Gln Ser Ser Arg Glu Lys Gln Lys Lys Asp Gln Arg Pro Leu Ser Thr
        690             695             700 act ggc acc agg cca cac aaa cag aag agg aaa ccc cag atg gta aag    2160
Thr Gly Thr Arg Pro His Lys Gln Lys Arg Lys Pro Gln Met Val Lys
705             710             715             720 gct gtt caa ccc caa gag atg agt cag atg aag ccc cat gtg tat gat    2208
Ala Val Gln Pro Gln Glu Met Ser Gln Met Lys Pro His Val Tyr Asp
            725             730             735
```

```
ctg cca gta gaa ggc aat gag ccc cca gcc tct ttt cat aaa gac aca    2256
Leu Pro Val Glu Gly Asn Glu Pro Pro Ala Ser Phe His Lys Asp Thr
            740                 745                 750 aac gca ctt ccc cct act gtt ttc aag gat aat cca gtg tct aca cct    2304
Asn Ala Leu Pro Pro Thr Val Phe Lys Asp Asn Pro Val Ser Thr Pro
        755                 760                 765 aag gac tca aat cca aaa gca tga                                    2328
Lys Asp Ser Asn Pro Lys Ala
    770                 775

<210> SEQ ID NO 2
<211> LENGTH: 775
<212> TYPE: PRT
<213> ORGANISM: Homo sapiens

<400> SEQUENCE: 2

Met Leu Gln Gly Leu Leu Pro Val Ser Leu Leu Ser Val Ala Val
1               5                   10                  15

Ser Ala Ile Lys Glu Leu Pro Gly Val Lys Lys Tyr Glu Val Val Tyr
                20                  25                  30

Pro Ile Arg Leu His Pro Leu His Lys Arg Glu Ala Lys Glu Pro Glu
            35                  40                  45

Gln Gln Glu Gln Phe Glu Thr Glu Leu Lys Tyr Lys Met Thr Ile Asn
        50                  55                  60

Gly Lys Ile Ala Val Leu Tyr Leu Lys Lys Asn Lys Asn Leu Leu Ala
65                  70                  75                  80

Pro Gly Tyr Thr Glu Thr Tyr Tyr Asn Ser Thr Gly Lys Glu Ile Thr
                85                  90                  95

Thr Ser Pro Gln Ile Met Asp Asp Cys Tyr Tyr Gln Gly His Ile Leu
            100                 105                 110

Asn Glu Lys Val Ser Asp Ala Ser Ile Ser Thr Cys Arg Gly Leu Arg
        115                 120                 125

Gly Tyr Phe Ser Gln Gly Asp Gln Arg Tyr Phe Ile Glu Pro Leu Ser
    130                 135                 140

Pro Ile His Arg Asp Gly Gln Glu His Ala Leu Phe Lys Tyr Asn Pro
145                 150                 155                 160

Asp Glu Lys Asn Tyr Asp Ser Thr Cys Gly Met Asp Gly Val Leu Trp
                165                 170                 175

Ala His Asp Leu Gln Gln Asn Ile Ala Leu Pro Ala Thr Lys Leu Val
            180                 185                 190

Lys Leu Lys Asp Arg Lys Val Gln Glu His Glu Lys Tyr Ile Glu Tyr
        195                 200                 205

Tyr Leu Val Leu Asp Asn Gly Glu Phe Lys Arg Tyr Asn Glu Asn Gln
    210                 215                 220

Asp Glu Ile Arg Lys Arg Val Phe Glu Met Ala Asn Tyr Val Asn Met
225                 230                 235                 240

Leu Tyr Lys Lys Leu Asn Thr His Val Ala Leu Val Gly Met Glu Ile
                245                 250                 255

Trp Thr Asp Lys Asp Lys Ile Lys Ile Thr Pro Asn Ala Ser Phe Thr
            260                 265                 270

Leu Glu Asn Phe Ser Lys Trp Arg Gly Ser Val Leu Ser Arg Arg Lys
        275                 280                 285

Arg His Asp Ile Ala Gln Leu Ile Thr Ala Thr Glu Leu Ala Gly Thr
    290                 295                 300

Thr Val Gly Leu Ala Phe Met Ser Thr Met Cys Ser Pro Tyr Ser Val
```

```
            305                 310                 315                 320
Gly Val Val Gln Asp His Ser Asp Asn Leu Leu Arg Val Ala Gly Thr
                325                 330                 335

Met Ala His Glu Met Gly His Asn Phe Gly Met Phe His Asp Asp Tyr
            340                 345                 350

Ser Cys Lys Cys Pro Ser Thr Ile Cys Val Met Asp Lys Ala Leu Ser
            355                 360                 365

Phe Tyr Ile Pro Thr Asp Phe Ser Ser Cys Ser Arg Leu Ser Tyr Asp
        370                 375                 380

Lys Phe Phe Glu Asp Lys Leu Ser Asn Cys Leu Phe Asn Ala Pro Leu
385                 390                 395                 400

Pro Thr Asp Ile Ile Ser Thr Pro Ile Cys Gly Asn Gln Leu Val Glu
                405                 410                 415

Met Gly Glu Asp Cys Asp Cys Gly Thr Ser Glu Cys Thr Asn Ile
            420                 425                 430

Cys Cys Asp Ala Lys Thr Cys Lys Ile Lys Ala Thr Phe Gln Cys Ala
            435                 440                 445

Leu Gly Glu Cys Cys Glu Lys Cys Gln Phe Lys Lys Ala Gly Met Val
        450                 455                 460

Cys Arg Pro Ala Lys Asp Glu Cys Asp Leu Pro Glu Met Cys Asn Gly
465                 470                 475                 480

Lys Ser Gly Asn Cys Pro Asp Asp Arg Phe Gln Val Asn Gly Phe Pro
                485                 490                 495

Cys His His Gly Lys Gly His Cys Leu Met Gly Thr Cys Pro Thr Leu
            500                 505                 510

Gln Glu Gln Cys Thr Glu Leu Trp Gly Pro Gly Thr Glu Val Ala Asp
            515                 520                 525

Lys Ser Cys Tyr Asn Arg Asn Glu Gly Gly Ser Lys Tyr Gly Tyr Cys
        530                 535                 540

Arg Arg Val Asp Asp Thr Leu Ile Pro Cys Lys Ala Asn Asp Thr Met
545                 550                 555                 560

Cys Gly Lys Leu Phe Cys Gln Gly Gly Ser Asp Asn Leu Pro Trp Lys
                565                 570                 575

Gly Arg Ile Val Thr Phe Leu Thr Cys Lys Thr Phe Asp Pro Glu Asp
            580                 585                 590

Thr Ser Gln Glu Ile Gly Met Val Ala Asn Gly Thr Lys Cys Gly Asp
            595                 600                 605

Asn Lys Val Cys Ile Asn Ala Glu Cys Val Asp Ile Glu Lys Ala Tyr
        610                 615                 620

Lys Ser Thr Asn Cys Ser Ser Lys Cys Lys Gly His Ala Val Cys Asp
625                 630                 635                 640

His Glu Leu Gln Cys Gln Cys Glu Glu Gly Trp Ile Pro Pro Asp Cys
                645                 650                 655

Asp Asp Ser Ser Val Val Phe His Phe Ser Ile Val Val Gly Val Leu
            660                 665                 670

Phe Pro Met Ala Val Ile Phe Val Val Ala Met Val Ile Arg His
            675                 680                 685

Gln Ser Ser Arg Glu Lys Gln Lys Lys Asp Gln Arg Pro Leu Ser Thr
        690                 695                 700

Thr Gly Thr Arg Pro His Lys Gln Lys Arg Lys Pro Gln Met Val Lys
705                 710                 715                 720

Ala Val Gln Pro Gln Glu Met Ser Gln Met Lys Pro His Val Tyr Asp
                725                 730                 735
```

```
Leu Pro Val Glu Gly Asn Glu Pro Ala Ser Phe His Lys Asp Thr
            740                 745                 750

Asn Ala Leu Pro Pro Thr Val Phe Lys Asp Asn Pro Val Ser Thr Pro
            755                 760                 765

Lys Asp Ser Asn Pro Lys Ala
    770             775

<210> SEQ ID NO 3
<211> LENGTH: 1623
<212> TYPE: DNA
<213> ORGANISM: Homo sapiens
<220> FEATURE:
<221> NAME/KEY: CDS
<222> LOCATION: (1)..(1623)

<400> SEQUENCE: 3 atg ttg caa ggt ctc ctg cca gtc agt ctc ctc ctc tct gtt gca gta    48
Met Leu Gln Gly Leu Leu Pro Val Ser Leu Leu Leu Ser Val Ala Val
1               5                   10                  15 agt gct ata aaa gaa ctc cct ggg gtg aag aag tat gaa gtg gtt tat    96
Ser Ala Ile Lys Glu Leu Pro Gly Val Lys Lys Tyr Glu Val Val Tyr
                20                  25                  30 cct ata aga ctt cat cca ctg cat aaa aga gag gcc aaa gag cca gag   144
Pro Ile Arg Leu His Pro Leu His Lys Arg Glu Ala Lys Glu Pro Glu
            35                  40                  45 caa cag gaa caa ttt gaa act gaa tta aag tat aaa atg aca att aat   192
Gln Gln Glu Gln Phe Glu Thr Glu Leu Lys Tyr Lys Met Thr Ile Asn
        50                  55                  60 gga aaa att gca gtg ctt tat ttg aaa aaa aac aag aac ctc ctt gca   240
Gly Lys Ile Ala Val Leu Tyr Leu Lys Lys Asn Lys Asn Leu Leu Ala
65                  70                  75                  80 cca ggc tac acg gaa aca tat tat aat tcc act gga aag gag atc acc   288
Pro Gly Tyr Thr Glu Thr Tyr Tyr Asn Ser Thr Gly Lys Glu Ile Thr
                85                  90                  95 aca agc cca caa att atg gat gat tgt tat tat caa gga cat att ctt   336
Thr Ser Pro Gln Ile Met Asp Asp Cys Tyr Tyr Gln Gly His Ile Leu
            100                 105                 110 aat gaa aag gtt tct gac gct agc atc agc aca tgt agg ggt cta agg   384
Asn Glu Lys Val Ser Asp Ala Ser Ile Ser Thr Cys Arg Gly Leu Arg
        115                 120                 125 ggc tac ttc agt cag ggg gat caa aga tac ttt att gaa cct tta agc   432
Gly Tyr Phe Ser Gln Gly Asp Gln Arg Tyr Phe Ile Glu Pro Leu Ser
    130                 135                 140 ccc ata cat cgg gat gga cag gag cat gca ctc ttc aag tat aac cct   480
Pro Ile His Arg Asp Gly Gln Glu His Ala Leu Phe Lys Tyr Asn Pro
145                 150                 155                 160 gat gaa aag aat tat gac agc acc tgt ggg atg gat ggt gtg ttg tgg   528
Asp Glu Lys Asn Tyr Asp Ser Thr Cys Gly Met Asp Gly Val Leu Trp
                165                 170                 175 gcc cac gat ttg cag cag aac att gcc cta cct gcc acc aaa cta gta   576
Ala His Asp Leu Gln Gln Asn Ile Ala Leu Pro Ala Thr Lys Leu Val
            180                 185                 190 aaa ttg aaa gac agg aag gtt cag gaa cat gag aaa tac ata gaa tat   624
Lys Leu Lys Asp Arg Lys Val Gln Glu His Glu Lys Tyr Ile Glu Tyr
        195                 200                 205 tat ttg gtc ctg gat aat ggt gag ttt aaa agg tac aat gag aat caa   672
Tyr Leu Val Leu Asp Asn Gly Glu Phe Lys Arg Tyr Asn Glu Asn Gln
    210                 215                 220 gat gag atc aga aag agg gta ttt gag atg gct aat tat gtc aac atg   720
Asp Glu Ile Arg Lys Arg Val Phe Glu Met Ala Asn Tyr Val Asn Met
```

```
                225                 230                 235                 240
ctt tat aaa aag ctc aat act cat gtg gcc tta gtt ggt atg gaa atc          768
Leu Tyr Lys Lys Leu Asn Thr His Val Ala Leu Val Gly Met Glu Ile
                    245                 250                 255 tgg act gac aag gat aag ata aag ata acc cca aat gca agc ttc acc          816
Trp Thr Asp Lys Asp Lys Ile Lys Ile Thr Pro Asn Ala Ser Phe Thr
        260                 265                 270 ttg gag aat ttt tct aaa tgg agg ggg agt gtt ctc tca aga aga aag          864
Leu Glu Asn Phe Ser Lys Trp Arg Gly Ser Val Leu Ser Arg Arg Lys
            275                 280                 285 cgt cat gat att gct cag tta atc aca gca aca gaa ctt gct gga acg          912
Arg His Asp Ile Ala Gln Leu Ile Thr Ala Thr Glu Leu Ala Gly Thr
    290                 295                 300 act gtg ggt ctt gca ttt atg tct aca atg tgt tct cct tat tct gtt          960
Thr Val Gly Leu Ala Phe Met Ser Thr Met Cys Ser Pro Tyr Ser Val
305                 310                 315                 320 ggc gtt gtt cag gac cac agc gat aat ctt ctt aga gtt gca ggg aca         1008
Gly Val Val Gln Asp His Ser Asp Asn Leu Leu Arg Val Ala Gly Thr
                325                 330                 335 atg gca cat gaa atg ggc cac aac ttt gga atg ttt cat gac gac tat         1056
Met Ala His Glu Met Gly His Asn Phe Gly Met Phe His Asp Asp Tyr
        340                 345                 350 tct tgc aag tgt cct tct aca ata tgt gtg atg gac aaa gca ctg agc         1104
Ser Cys Lys Cys Pro Ser Thr Ile Cys Val Met Asp Lys Ala Leu Ser
            355                 360                 365 ttc tat ata ccc aca gac ttc agt tcc tgc agc cgt ctc agc tat gac         1152
Phe Tyr Ile Pro Thr Asp Phe Ser Ser Cys Ser Arg Leu Ser Tyr Asp
    370                 375                 380 aag ttt ttt gaa gat aaa tta tca aat tgc ctc ttt aat gct cca ttg         1200
Lys Phe Phe Glu Asp Lys Leu Ser Asn Cys Leu Phe Asn Ala Pro Leu
385                 390                 395                 400 cct aca gat atc ata tcc act cca att tgt ggg aac cag ttg gtg gaa         1248
Pro Thr Asp Ile Ile Ser Thr Pro Ile Cys Gly Asn Gln Leu Val Glu
                405                 410                 415 atg gga gag gac tgt gat tgt ggg aca tct gag gaa tgt acc aat att         1296
Met Gly Glu Asp Cys Asp Cys Gly Thr Ser Glu Glu Cys Thr Asn Ile
        420                 425                 430 tgc tgt gat gct aag aca tgt aaa atc aaa gca act ttt caa tgt gca         1344
Cys Cys Asp Ala Lys Thr Cys Lys Ile Lys Ala Thr Phe Gln Cys Ala
            435                 440                 445 tta gga gaa tgt tgt gaa aaa tgc caa ttt aaa aag gct ggg atg gtg         1392
Leu Gly Glu Cys Cys Glu Lys Cys Gln Phe Lys Lys Ala Gly Met Val
    450                 455                 460 tgc aga cca gca aaa gat gag tgc gac ctg cct gaa atg tgt aat ggt         1440
Cys Arg Pro Ala Lys Asp Glu Cys Asp Leu Pro Glu Met Cys Asn Gly
465                 470                 475                 480 aaa tct ggt aat tgt cct gat gat aga ttc caa gtc aat ggc ttc cct         1488
Lys Ser Gly Asn Cys Pro Asp Asp Arg Phe Gln Val Asn Gly Phe Pro
                485                 490                 495 tgc cat cac ggg aag ggc cac tgc ttg atg ggg aca tgc ccc aca ctg         1536
Cys His His Gly Lys Gly His Cys Leu Met Gly Thr Cys Pro Thr Leu
        500                 505                 510 cag gag cag tgc aca gag ctg tgg gga cca ggt agg agg aca aat cct         1584
Gln Glu Gln Cys Thr Glu Leu Trp Gly Pro Gly Arg Arg Thr Asn Pro
            515                 520                 525 ttc ccc tgt gca tgt gcg aag gaa aat cat ttc aga tga                     1623
Phe Pro Cys Ala Cys Ala Lys Glu Asn His Phe Arg
    530                 535                 540
```

-continued

```
<210> SEQ ID NO 4
<211> LENGTH: 540
<212> TYPE: PRT
<213> ORGANISM: Homo sapiens

<400> SEQUENCE: 4

Met Leu Gln Gly Leu Leu Pro Val Ser Leu Leu Ser Val Ala Val
1               5                   10                  15

Ser Ala Ile Lys Glu Leu Pro Gly Val Lys Lys Tyr Glu Val Tyr
                20                  25                  30

Pro Ile Arg Leu His Pro Leu His Lys Arg Glu Ala Lys Glu Pro
            35                  40                  45

Gln Gln Glu Gln Phe Glu Thr Glu Leu Lys Tyr Lys Met Thr Ile Asn
50                  55                  60

Gly Lys Ile Ala Val Leu Tyr Leu Lys Asn Lys Asn Leu Leu Ala
65                  70                  75                  80

Pro Gly Tyr Thr Glu Thr Tyr Tyr Asn Ser Thr Gly Lys Glu Ile Thr
                85                  90                  95

Thr Ser Pro Gln Ile Met Asp Asp Cys Tyr Tyr Gln Gly His Ile Leu
            100                 105                 110

Asn Glu Lys Val Ser Asp Ala Ser Ile Ser Thr Cys Arg Gly Leu Arg
        115                 120                 125

Gly Tyr Phe Ser Gln Gly Asp Gln Arg Tyr Phe Ile Glu Pro Leu Ser
    130                 135                 140

Pro Ile His Arg Asp Gly Gln Glu His Ala Leu Phe Lys Tyr Asn Pro
145                 150                 155                 160

Asp Glu Lys Asn Tyr Asp Ser Thr Cys Gly Met Asp Gly Val Leu Trp
                165                 170                 175

Ala His Asp Leu Gln Gln Asn Ile Ala Leu Pro Ala Thr Lys Leu Val
            180                 185                 190

Lys Leu Lys Asp Arg Lys Val Gln Glu His Glu Lys Tyr Ile Glu Tyr
        195                 200                 205

Tyr Leu Val Leu Asp Asn Gly Glu Phe Lys Arg Tyr Asn Glu Asn Gln
    210                 215                 220

Asp Glu Ile Arg Lys Arg Val Phe Glu Met Ala Asn Tyr Val Asn Met
225                 230                 235                 240

Leu Tyr Lys Lys Leu Asn Thr His Val Ala Leu Val Gly Met Glu Ile
                245                 250                 255

Trp Thr Asp Lys Asp Lys Ile Lys Ile Thr Pro Asn Ala Ser Phe Thr
            260                 265                 270

Leu Glu Asn Phe Ser Lys Trp Arg Gly Ser Val Leu Ser Arg Arg Lys
        275                 280                 285

Arg His Asp Ile Ala Gln Leu Ile Thr Ala Thr Glu Leu Ala Gly Thr
    290                 295                 300

Thr Val Gly Leu Ala Phe Met Ser Thr Met Cys Ser Pro Tyr Ser Val
305                 310                 315                 320

Gly Val Val Gln Asp His Ser Asp Asn Leu Leu Arg Val Ala Gly Thr
                325                 330                 335

Met Ala His Glu Met Gly His Asn Phe Gly Met Phe His Asp Asp Tyr
            340                 345                 350

Ser Cys Lys Cys Pro Ser Thr Ile Cys Val Met Asp Lys Ala Leu Ser
        355                 360                 365

Phe Tyr Ile Pro Thr Asp Phe Ser Ser Cys Ser Arg Leu Ser Tyr Asp
    370                 375                 380
```

```
Lys Phe Phe Glu Asp Lys Leu Ser Asn Cys Leu Phe Asn Ala Pro Leu
385                 390                 395                 400

Pro Thr Asp Ile Ile Ser Thr Pro Ile Cys Gly Asn Gln Leu Val Glu
            405                 410                 415

Met Gly Glu Asp Cys Asp Cys Gly Thr Ser Glu Glu Cys Thr Asn Ile
        420                 425                 430

Cys Cys Asp Ala Lys Thr Cys Lys Ile Lys Ala Thr Phe Gln Cys Ala
        435                 440                 445

Leu Gly Glu Cys Cys Glu Lys Cys Gln Phe Lys Lys Ala Gly Met Val
    450                 455                 460

Cys Arg Pro Ala Lys Asp Glu Cys Asp Leu Pro Glu Met Cys Asn Gly
465                 470                 475                 480

Lys Ser Gly Asn Cys Pro Asp Asp Arg Phe Gln Val Asn Gly Phe Pro
                485                 490                 495

Cys His His Gly Lys Gly His Cys Leu Met Gly Thr Cys Pro Thr Leu
            500                 505                 510

Gln Glu Gln Cys Thr Glu Leu Trp Gly Pro Gly Arg Arg Thr Asn Pro
            515                 520                 525

Phe Pro Cys Ala Cys Ala Lys Glu Asn His Phe Arg
530                 535                 540

<210> SEQ ID NO 5
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 5

Arg Ser Ser Gln Asn Ile Ile His Ser Asp Gly Asn Thr Tyr Leu Glu
1               5                   10                  15

<210> SEQ ID NO 6
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 6

Lys Val Ser Asn Arg Phe Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 7

Leu Gln Gly Ser His Val Pro Trp Thr
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 8
```

```
Ser Tyr Gly Ile Ser
1               5
```

<210> SEQ ID NO 9
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 9

```
Glu Ile Tyr Pro Arg Ser Gly Asn Thr Tyr Tyr Asn Glu Lys Phe Lys
1               5                   10                  15
Gly
```

<210> SEQ ID NO 10
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 10

```
Glu Asn Val Tyr Ser Ser Asn Tyr Gly Phe Ala Phe
1               5                   10
```

<210> SEQ ID NO 11
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 11

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Ile His Ser
            20                  25                  30

Asp Gly Asn Thr Tyr Leu Glu Trp Tyr Leu Gln Lys Pro Gly Gln Ser
        35                  40                  45

Pro Lys Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Gly
                85                  90                  95

Ser His Val Pro Trp Thr Phe Gly Gly Gly Thr Lys Leu Glu Ile Lys
            100                 105                 110

Arg Ala
```

<210> SEQ ID NO 12
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 12

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30
```

Gly Ile Ser Trp Val Lys Gln Arg Thr Gly Gln Gly Leu Glu Trp Ile
            35                  40                  45

Gly Glu Ile Tyr Pro Arg Ser Gly Asn Thr Tyr Tyr Asn Glu Lys Phe
        50                  55                  60

Lys Gly Lys Ala Thr Leu Thr Ala Asp Lys Ser Ser Thr Ala Tyr
65                  70                  75                  80

Met Glu Leu Arg Arg Leu Thr Ser Glu Asp Ser Ala Val Phe Phe Cys
                85                  90                  95

Ala Arg Glu Asn Val Tyr Ser Ser Asn Tyr Gly Phe Ala Phe Trp Gly
                100                 105                 110

Gln Gly Thr Leu Val Thr Val Ser Ala
        115                 120

<210> SEQ ID NO 13
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 13

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 14
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 14

Trp Tyr Leu Gln Lys Pro Gly Gln Ser Pro Lys Phe Leu Ile Tyr
1               5                   10                  15

<210> SEQ ID NO 15
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 15

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 16
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 16

Phe Gly Gly Gly Thr Lys Leu Glu Ile Lys Arg Ala
1               5                   10

<210> SEQ ID NO 17

```
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 17

Gln Val Gln Leu Gln Gln Ser Gly Ala Glu Leu Ala Arg Pro Gly Ala
1               5                   10                  15
Ser Val Lys Leu Ser Cys Lys Ala Ser Gly Tyr Thr Phe Thr
            20                  25                  30

<210> SEQ ID NO 18
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 18

Trp Val Lys Gln Arg Thr Gly Gln Gly Leu Glu Trp Ile Gly
1               5                   10

<210> SEQ ID NO 19
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 19

Lys Ala Thr Leu Thr Ala Asp Lys Ser Ser Ser Thr Ala Tyr Met Glu
1               5                   10                  15
Leu Arg Arg Leu Thr Ser Glu Asp Ser Ala Val Phe Phe Cys Ala Arg
            20                  25                  30

<210> SEQ ID NO 20
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 20

Trp Gly Gln Gly Thr Leu Val Thr Val Ser Ala
1               5                   10

<210> SEQ ID NO 21
<211> LENGTH: 1734
<212> TYPE: DNA
<213> ORGANISM: Homo sapiens
<220> FEATURE:
<221> NAME/KEY: CDS
<222> LOCATION: (1)..(1734)

<400> SEQUENCE: 21 gtt cag gaa cat gag aaa tac ata gaa tat tat ttg gtc ctg gat aat      48
Val Gln Glu His Glu Lys Tyr Ile Glu Tyr Tyr Leu Val Leu Asp Asn
1               5                   10                  15 ggt gag ttt aaa agg tac aat gag aat caa gat gag atc aga aag agg      96
Gly Glu Phe Lys Arg Tyr Asn Glu Asn Gln Asp Glu Ile Arg Lys Arg
            20                  25                  30 gta ttt gag atg gct aat tat gtc aac atg ctt tat aaa aag ctc aat     144
Val Phe Glu Met Ala Asn Tyr Val Asn Met Leu Tyr Lys Lys Leu Asn
        35                  40                  45
```

| | | |
|---|---|---|
| act cat gtg gcc tta gtt ggt atg gaa atc tgg act gac aag gat aag<br>Thr His Val Ala Leu Val Gly Met Glu Ile Trp Thr Asp Lys Asp Lys<br>     50                      55                      60 | | 192 |
| ata aag ata acc cca aat gca agc ttc acc ttg gag aat ttt tct aaa<br>Ile Lys Ile Thr Pro Asn Ala Ser Phe Thr Leu Glu Asn Phe Ser Lys<br>65                    70                      75                    80 | | 240 |
| tgg agg ggg agt gtt ctc tca aga aga aag cgt cat gat att gct cag<br>Trp Arg Gly Ser Val Leu Ser Arg Arg Lys Arg His Asp Ile Ala Gln<br>                  85                      90                      95 | | 288 |
| tta atc aca gca aca gaa ctt gct gga acg act gtg ggt ctt gca ttt<br>Leu Ile Thr Ala Thr Glu Leu Ala Gly Thr Thr Val Gly Leu Ala Phe<br>                100                    105                    110 | | 336 |
| atg tct aca atg tgt tct cct tat tct gtt ggc gtt gtt cag gac cac<br>Met Ser Thr Met Cys Ser Pro Tyr Ser Val Gly Val Val Gln Asp His<br>               115                    120                    125 | | 384 |
| agc gat aat ctt ctt aga gtt gca ggg aca atg gca cat gaa atg ggc<br>Ser Asp Asn Leu Leu Arg Val Ala Gly Thr Met Ala His Glu Met Gly<br>130                    135                    140 | | 432 |
| cac aac ttt gga atg ttt cat gac gac tat tct tgc aag tgt cct tct<br>His Asn Phe Gly Met Phe His Asp Asp Tyr Ser Cys Lys Cys Pro Ser<br>145                    150                    155                    160 | | 480 |
| aca ata tgt gtg atg gac aaa gca ctg agc ttc tat ata ccc aca gac<br>Thr Ile Cys Val Met Asp Lys Ala Leu Ser Phe Tyr Ile Pro Thr Asp<br>                    165                    170                    175 | | 528 |
| ttc agt tcc tgc agc cgt ctc agc tat gac aag ttt ttt gaa gat aaa<br>Phe Ser Ser Cys Ser Arg Leu Ser Tyr Asp Lys Phe Phe Glu Asp Lys<br>                  180                    185                    190 | | 576 |
| tta tca aat tgc ctc ttt aat gct cca ttg cct aca gat atc ata tcc<br>Leu Ser Asn Cys Leu Phe Asn Ala Pro Leu Pro Thr Asp Ile Ile Ser<br>                195                    200                    205 | | 624 |
| act cca att tgt ggg aac cag ttg gtg gaa atg gga gag gac tgt gat<br>Thr Pro Ile Cys Gly Asn Gln Leu Val Glu Met Gly Glu Asp Cys Asp<br>210                    215                    220 | | 672 |
| tgt ggg aca tct gag gaa tgt acc aat att tgc tgt gat gct aag aca<br>Cys Gly Thr Ser Glu Glu Cys Thr Asn Ile Cys Cys Asp Ala Lys Thr<br>225                    230                    235                    240 | | 720 |
| tgt aaa atc aaa gca act ttt caa tgt gca tta gga gaa tgt tgt gaa<br>Cys Lys Ile Lys Ala Thr Phe Gln Cys Ala Leu Gly Glu Cys Cys Glu<br>                  245                    250                    255 | | 768 |
| aaa tgc caa ttt aaa aag gct ggg atg gtg tgc aga cca gca aaa gat<br>Lys Cys Gln Phe Lys Lys Ala Gly Met Val Cys Arg Pro Ala Lys Asp<br>                260                    265                    270 | | 816 |
| gag tgc gac ctg cct gaa atg tgt aat ggt aaa tct ggt aat tgt cct<br>Glu Cys Asp Leu Pro Glu Met Cys Asn Gly Lys Ser Gly Asn Cys Pro<br>                275                    280                    285 | | 864 |
| gat gat aga ttc caa gtc aat ggc ttc cct tgc cat cac ggg aag ggc<br>Asp Asp Arg Phe Gln Val Asn Gly Phe Pro Cys His His Gly Lys Gly<br>290                    295                    300 | | 912 |
| cac tgc ttg atg ggg aca tgc ccc aca ctg cag gag cag tgc aca gag<br>His Cys Leu Met Gly Thr Cys Pro Thr Leu Gln Glu Gln Cys Thr Glu<br>305                    310                    315                    320 | | 960 |
| ctg tgg gga cca gga act gag gtt gca gat aag tca tgt tac aac agg<br>Leu Trp Gly Pro Gly Thr Glu Val Ala Asp Lys Ser Cys Tyr Asn Arg<br>                325                    330                    335 | | 1008 |
| aat gaa ggt ggg tca aag tac ggg tac tgt cgc aga gtg gat gac aca<br>Asn Glu Gly Gly Ser Lys Tyr Gly Tyr Cys Arg Arg Val Asp Asp Thr<br>                  340                    345                    350 | | 1056 |
| ctc att ccc tgc aaa gca aat gat acc atg tgt ggg aag ttg ttc tgt<br>Leu Ile Pro Cys Lys Ala Asn Asp Thr Met Cys Gly Lys Leu Phe Cys<br>                355                    360                    365 | | 1104 |

| | | | | | | | | | | | | | | | |
|---|---|---|---|---|---|---|---|---|---|---|---|---|---|---|---|
| caa | ggt | ggg | tcg | gat | aat | ttg | ccc | tgg | aaa | gga | cgg | ata | gtg | act | ttc | 1152 |
| Gln | Gly | Gly | Ser | Asp | Asn | Leu | Pro | Trp | Lys | Gly | Arg | Ile | Val | Thr | Phe |
| | 370 | | | | 375 | | | | | 380 | | | | | |

```
caa ggt ggg tcg gat aat ttg ccc tgg aaa gga cgg ata gtg act ttc    1152
Gln Gly Gly Ser Asp Asn Leu Pro Trp Lys Gly Arg Ile Val Thr Phe
    370             375                 380 ctg aca tgt aaa aca ttt gat cct gaa gac aca agt caa gaa ata ggc    1200
Leu Thr Cys Lys Thr Phe Asp Pro Glu Asp Thr Ser Gln Glu Ile Gly
385             390                 395                 400 atg gtg gcc aat gga act aag tgt ggc gat aac aag gtt tgc att aat    1248
Met Val Ala Asn Gly Thr Lys Cys Gly Asp Asn Lys Val Cys Ile Asn
                405                 410                 415 gca gaa tgt gtg gat att gag aaa gcc tac aaa tca acc aat tgc tca    1296
Ala Glu Cys Val Asp Ile Glu Lys Ala Tyr Lys Ser Thr Asn Cys Ser
            420                 425                 430 tct aag tgc aaa gga cat gct gtg tgt gac cat gag ctc cag tgt caa    1344
Ser Lys Cys Lys Gly His Ala Val Cys Asp His Glu Leu Gln Cys Gln
        435                 440                 445 tgt gag gaa gga tgg atc cct ccc gac tgc gat gac tcc tca gtg gtc    1392
Cys Glu Glu Gly Trp Ile Pro Pro Asp Cys Asp Asp Ser Ser Val Val
    450                 455                 460 ttc cac ttc tcc att gtg gtt ggg gtg ctg ttc cca atg gcg gtc att    1440
Phe His Phe Ser Ile Val Val Gly Val Leu Phe Pro Met Ala Val Ile
465                 470                 475                 480 ttt gtg gtg gtt gct atg gta atc cgg cac cag agc tcc aga gaa aag    1488
Phe Val Val Val Ala Met Val Ile Arg His Gln Ser Ser Arg Glu Lys
                485                 490                 495 cag aag aaa gat cag agg cca cta tct acc act ggc acc agg cca cac    1536
Gln Lys Lys Asp Gln Arg Pro Leu Ser Thr Thr Gly Thr Arg Pro His
            500                 505                 510 aaa cag aag agg aaa ccc cag atg gta aag gct gtt caa ccc caa gag    1584
Lys Gln Lys Arg Lys Pro Gln Met Val Lys Ala Val Gln Pro Gln Glu
        515                 520                 525 atg agt cag atg aag ccc cat gtg tat gat ctg cca gta gaa ggc aat    1632
Met Ser Gln Met Lys Pro His Val Tyr Asp Leu Pro Val Glu Gly Asn
    530                 535                 540 gag ccc cca gcc tct ttt cat aaa gac aca aac gca ctt ccc cct act    1680
Glu Pro Pro Ala Ser Phe His Lys Asp Thr Asn Ala Leu Pro Pro Thr
545                 550                 555                 560 gtt ttc aag gat aat cca gtg tct aca cct aag gac tca aat cca aaa    1728
Val Phe Lys Asp Asn Pro Val Ser Thr Pro Lys Asp Ser Asn Pro Lys
                565                 570                 575 gca tga                                                            1734
Ala
```

<210> SEQ ID NO 22
<211> LENGTH: 577
<212> TYPE: PRT
<213> ORGANISM: Homo sapiens

<400> SEQUENCE: 22

```
Val Gln Glu His Glu Lys Tyr Ile Glu Tyr Tyr Leu Val Leu Asp Asn
1               5                   10                  15

Gly Glu Phe Lys Arg Tyr Asn Glu Asn Gln Asp Glu Ile Arg Lys Arg
                20                  25                  30

Val Phe Glu Met Ala Asn Tyr Val Asn Met Leu Tyr Lys Lys Leu Asn
            35                  40                  45

Thr His Val Ala Leu Val Gly Met Glu Ile Trp Thr Asp Lys Asp Lys
        50                  55                  60

Ile Lys Ile Thr Pro Asn Ala Ser Phe Thr Leu Glu Asn Phe Ser Lys
65                  70                  75                  80
```

```
Trp Arg Gly Ser Val Leu Ser Arg Arg Lys Arg His Asp Ile Ala Gln
                85                  90                  95
Leu Ile Thr Ala Thr Glu Leu Ala Gly Thr Thr Val Gly Leu Ala Phe
            100                 105                 110
Met Ser Thr Met Cys Ser Pro Tyr Ser Val Gly Val Gln Asp His
            115                 120                 125
Ser Asp Asn Leu Leu Arg Val Ala Gly Thr Met Ala His Glu Met Gly
130                 135                 140
His Asn Phe Gly Met Phe His Asp Asp Tyr Ser Cys Lys Cys Pro Ser
145                 150                 155                 160
Thr Ile Cys Val Met Asp Lys Ala Leu Ser Phe Tyr Ile Pro Thr Asp
                165                 170                 175
Phe Ser Ser Cys Ser Arg Leu Ser Tyr Asp Lys Phe Phe Glu Asp Lys
            180                 185                 190
Leu Ser Asn Cys Leu Phe Asn Ala Pro Leu Pro Thr Asp Ile Ile Ser
            195                 200                 205
Thr Pro Ile Cys Gly Asn Gln Leu Val Glu Met Gly Glu Asp Cys Asp
    210                 215                 220
Cys Gly Thr Ser Glu Glu Cys Thr Asn Ile Cys Cys Asp Ala Lys Thr
225                 230                 235                 240
Cys Lys Ile Lys Ala Thr Phe Gln Cys Ala Leu Gly Glu Cys Cys Glu
                245                 250                 255
Lys Cys Gln Phe Lys Lys Ala Gly Met Val Cys Arg Pro Ala Lys Asp
            260                 265                 270
Glu Cys Asp Leu Pro Glu Met Cys Asn Gly Lys Ser Gly Asn Cys Pro
            275                 280                 285
Asp Asp Arg Phe Gln Val Asn Gly Phe Pro Cys His His Gly Lys Gly
    290                 295                 300
His Cys Leu Met Gly Thr Cys Pro Thr Leu Gln Glu Gln Cys Thr Glu
305                 310                 315                 320
Leu Trp Gly Pro Gly Thr Glu Val Ala Asp Lys Ser Cys Tyr Asn Arg
                325                 330                 335
Asn Glu Gly Gly Ser Lys Tyr Gly Tyr Cys Arg Arg Val Asp Asp Thr
            340                 345                 350
Leu Ile Pro Cys Lys Ala Asn Asp Thr Met Cys Gly Lys Leu Phe Cys
            355                 360                 365
Gln Gly Gly Ser Asp Asn Leu Pro Trp Lys Gly Arg Ile Val Thr Phe
    370                 375                 380
Leu Thr Cys Lys Thr Phe Asp Pro Glu Asp Thr Ser Gln Glu Ile Gly
385                 390                 395                 400
Met Val Ala Asn Gly Thr Lys Cys Gly Asp Asn Lys Val Cys Ile Asn
                405                 410                 415
Ala Glu Cys Val Asp Ile Glu Lys Ala Tyr Lys Ser Thr Asn Cys Ser
            420                 425                 430
Ser Lys Cys Lys Gly His Ala Val Cys Asp His Glu Leu Gln Cys Gln
            435                 440                 445
Cys Glu Glu Gly Trp Ile Pro Pro Asp Cys Asp Asp Ser Ser Val Val
    450                 455                 460
Phe His Phe Ser Ile Val Gly Val Leu Phe Pro Met Ala Val Ile
465                 470                 475                 480
Phe Val Val Val Ala Met Val Ile Arg His Gln Ser Ser Arg Glu Lys
                485                 490                 495
Gln Lys Lys Asp Gln Arg Pro Leu Ser Thr Thr Gly Thr Arg Pro His
```

```
                500               505               510
    Lys Gln Lys Arg Lys Pro Gln Met Val Lys Ala Val Gln Pro Gln Glu
            515               520               525

Met Ser Gln Met Lys Pro His Val Tyr Asp Leu Pro Val Glu Gly Asn
            530               535               540

Glu Pro Pro Ala Ser Phe His Lys Asp Thr Asn Ala Leu Pro Pro Thr
    545               550               555               560

Val Phe Lys Asp Asn Pro Val Ser Thr Pro Lys Asp Ser Asn Pro Lys
                    565               570               575

Ala

<210> SEQ ID NO 23
<211> LENGTH: 1029
<212> TYPE: DNA
<213> ORGANISM: Homo sapiens
<220> FEATURE:
<221> NAME/KEY: CDS
<222> LOCATION: (1)..(1029)

<400> SEQUENCE: 23 gtt cag gaa cat gag aaa tac ata gaa tat tat ttg gtc ctg gat aat     48
Val Gln Glu His Glu Lys Tyr Ile Glu Tyr Tyr Leu Val Leu Asp Asn
1               5                  10                  15 ggt gag ttt aaa agg tac aat gag aat caa gat gag atc aga aag agg     96
Gly Glu Phe Lys Arg Tyr Asn Glu Asn Gln Asp Glu Ile Arg Lys Arg
                20                  25                  30 gta ttt gag atg gct aat tat gtc aac atg ctt tat aaa aag ctc aat    144
Val Phe Glu Met Ala Asn Tyr Val Asn Met Leu Tyr Lys Lys Leu Asn
            35                  40                  45 act cat gtg gcc tta gtt ggt atg gaa atc tgg act gac aag gat aag    192
Thr His Val Ala Leu Val Gly Met Glu Ile Trp Thr Asp Lys Asp Lys
        50                  55                  60 ata aag ata acc cca aat gca agc ttc acc ttg gag aat ttt tct aaa    240
Ile Lys Ile Thr Pro Asn Ala Ser Phe Thr Leu Glu Asn Phe Ser Lys
65                  70                  75                  80 tgg agg ggg agt gtt ctc tca aga aga aag cgt cat gat att gct cag    288
Trp Arg Gly Ser Val Leu Ser Arg Arg Lys Arg His Asp Ile Ala Gln
                85                  90                  95 tta atc aca gca aca gaa ctt gct gga acg act gtg ggt ctt gca ttt    336
Leu Ile Thr Ala Thr Glu Leu Ala Gly Thr Thr Val Gly Leu Ala Phe
            100                 105                 110 atg tct aca atg tgt tct cct tat tct gtt ggc gtt gtt cag gac cac    384
Met Ser Thr Met Cys Ser Pro Tyr Ser Val Gly Val Val Gln Asp His
        115                 120                 125 agc gat aat ctt ctt aga gtt gca ggg aca atg gca cat gaa atg ggc    432
Ser Asp Asn Leu Leu Arg Val Ala Gly Thr Met Ala His Glu Met Gly
130                 135                 140 cac aac ttt gga atg ttt cat gac gac tat tct tgc aag tgt cct tct    480
His Asn Phe Gly Met Phe His Asp Asp Tyr Ser Cys Lys Cys Pro Ser
145                 150                 155                 160 aca ata tgt gtg atg gac aaa gca ctg agc ttc tat ata ccc aca gac    528
Thr Ile Cys Val Met Asp Lys Ala Leu Ser Phe Tyr Ile Pro Thr Asp
                165                 170                 175 ttc agt tcc tgc agc cgt ctc agc tat gac aag ttt ttt gaa gat aaa    576
Phe Ser Ser Cys Ser Arg Leu Ser Tyr Asp Lys Phe Phe Glu Asp Lys
            180                 185                 190 tta tca aat tgc ctc ttt aat gct cca ttg cct aca gat atc ata tcc    624
Leu Ser Asn Cys Leu Phe Asn Ala Pro Leu Pro Thr Asp Ile Ile Ser
        195                 200                 205
```

```
act cca att tgt ggg aac cag ttg gtg gaa atg gga gag gac tgt gat      672
Thr Pro Ile Cys Gly Asn Gln Leu Val Glu Met Gly Glu Asp Cys Asp
    210                 215                 220 tgt ggg aca tct gag gaa tgt acc aat att tgc tgt gat gct aag aca      720
Cys Gly Thr Ser Glu Glu Cys Thr Asn Ile Cys Cys Asp Ala Lys Thr
225                 230                 235                 240 tgt aaa atc aaa gca act ttt caa tgt gca tta gga gaa tgt tgt gaa      768
Cys Lys Ile Lys Ala Thr Phe Gln Cys Ala Leu Gly Glu Cys Cys Glu
                245                 250                 255 aaa tgc caa ttt aaa aag gct ggg atg gtg tgc aga cca gca aaa gat      816
Lys Cys Gln Phe Lys Lys Ala Gly Met Val Cys Arg Pro Ala Lys Asp
            260                 265                 270 gag tgc gac ctg cct gaa atg tgt aat ggt aaa tct ggt aat tgt cct      864
Glu Cys Asp Leu Pro Glu Met Cys Asn Gly Lys Ser Gly Asn Cys Pro
        275                 280                 285 gat gat aga ttc caa gtc aat ggc ttc cct tgc cat cac ggg aag ggc      912
Asp Asp Arg Phe Gln Val Asn Gly Phe Pro Cys His His Gly Lys Gly
    290                 295                 300 cac tgc ttg atg ggg aca tgc ccc aca ctg cag gag cag tgc aca gag      960
His Cys Leu Met Gly Thr Cys Pro Thr Leu Gln Glu Gln Cys Thr Glu
305                 310                 315                 320 ctg tgg gga cca ggt agg agg aca aat cct ttc ccc tgt gca tgt gcg     1008
Leu Trp Gly Pro Gly Arg Arg Thr Asn Pro Phe Pro Cys Ala Cys Ala
                325                 330                 335 aag gaa aat cat ttc aga tga                                         1029
Lys Glu Asn His Phe Arg
            340

<210> SEQ ID NO 24
<211> LENGTH: 342
<212> TYPE: PRT
<213> ORGANISM: Homo sapiens

<400> SEQUENCE: 24

Val Gln Glu His Glu Lys Tyr Ile Glu Tyr Tyr Leu Val Leu Asp Asn
1               5                   10                  15

Gly Glu Phe Lys Arg Tyr Asn Glu Asn Gln Asp Glu Ile Arg Lys Arg
            20                  25                  30

Val Phe Glu Met Ala Asn Tyr Val Asn Met Leu Tyr Lys Lys Leu Asn
        35                  40                  45

Thr His Val Ala Leu Val Gly Met Glu Ile Trp Thr Asp Lys Asp Lys
    50                  55                  60

Ile Lys Ile Thr Pro Asn Ala Ser Phe Thr Leu Glu Asn Phe Ser Lys
65                  70                  75                  80

Trp Arg Gly Ser Val Leu Ser Arg Arg Lys Arg His Asp Ile Ala Gln
                85                  90                  95

Leu Ile Thr Ala Thr Glu Leu Ala Gly Thr Thr Val Gly Leu Ala Phe
            100                 105                 110

Met Ser Thr Met Cys Ser Pro Tyr Ser Val Gly Val Gln Asp His
        115                 120                 125

Ser Asp Asn Leu Leu Arg Val Ala Gly Thr Met Ala His Glu Met Gly
    130                 135                 140

His Asn Phe Gly Met Phe His Asp Asp Tyr Ser Cys Lys Cys Pro Ser
145                 150                 155                 160

Thr Ile Cys Val Met Asp Lys Ala Leu Ser Phe Tyr Ile Pro Thr Asp
                165                 170                 175

Phe Ser Ser Cys Ser Arg Leu Ser Tyr Asp Lys Phe Phe Glu Asp Lys
            180                 185                 190
```

```
Leu Ser Asn Cys Leu Phe Asn Ala Pro Leu Pro Thr Asp Ile Ile Ser
        195                 200                 205

Thr Pro Ile Cys Gly Asn Gln Leu Val Glu Met Gly Glu Asp Cys Asp
210                 215                 220

Cys Gly Thr Ser Glu Glu Cys Thr Asn Ile Cys Cys Asp Ala Lys Thr
225                 230                 235                 240

Cys Lys Ile Lys Ala Thr Phe Gln Cys Ala Leu Gly Glu Cys Cys Glu
            245                 250                 255

Lys Cys Gln Phe Lys Lys Ala Gly Met Val Cys Arg Pro Ala Lys Asp
        260                 265                 270

Glu Cys Asp Leu Pro Glu Met Cys Asn Gly Lys Ser Gly Asn Cys Pro
    275                 280                 285

Asp Asp Arg Phe Gln Val Asn Gly Phe Pro Cys His His Gly Lys Gly
290                 295                 300

His Cys Leu Met Gly Thr Cys Pro Thr Leu Gln Glu Gln Cys Thr Glu
305                 310                 315                 320

Leu Trp Gly Pro Gly Arg Arg Thr Asn Pro Phe Pro Cys Ala Cys Ala
            325                 330                 335

Lys Glu Asn His Phe Arg
        340

<210> SEQ ID NO 25
<211> LENGTH: 2325
<212> TYPE: DNA
<213> ORGANISM: Mus musculus
<220> FEATURE:
<221> NAME/KEY: CDS
<222> LOCATION: (1)..(2325)

<400> SEQUENCE: 25 atg cag caa tgg agt ctt ctg gta gtc tct ttc ctt ctt tct cca gtt      48
Met Gln Gln Trp Ser Leu Leu Val Val Ser Phe Leu Leu Ser Pro Val
1               5                   10                  15 cca gta agt gca ata aaa gaa ctc cct aaa gcc aag aaa tat gaa gtg      96
Pro Val Ser Ala Ile Lys Glu Leu Pro Lys Ala Lys Lys Tyr Glu Val
                20                  25                  30 gtt tat ccc ata aga ctt cat cca ttg cgt aaa aga gag acc caa gag     144
Val Tyr Pro Ile Arg Leu His Pro Leu Arg Lys Arg Glu Thr Gln Glu
            35                  40                  45 cca gag cca aag gaa aca ttt gaa act gag cta agg tac aaa atg aca     192
Pro Glu Pro Lys Glu Thr Phe Glu Thr Glu Leu Arg Tyr Lys Met Thr
        50                  55                  60 gta aat gga aag gtt gct gtg ctg tat ctg aag aag aac aac aag ctc     240
Val Asn Gly Lys Val Ala Val Leu Tyr Leu Lys Lys Asn Asn Lys Leu
65                  70                  75                  80 ctt gcg cct gac tac tcg gaa aca tac tat aat tcc agt gga aac aag     288
Leu Ala Pro Asp Tyr Ser Glu Thr Tyr Tyr Asn Ser Ser Gly Asn Lys
                85                  90                  95 gtc acc aca agc ccg caa atc atg gat agc tgt tac tac caa gga cac     336
Val Thr Thr Ser Pro Gln Ile Met Asp Ser Cys Tyr Tyr Gln Gly His
                100                 105                 110 atc gta aat gag aaa gtt tct gca gcc agc atc agc acc tgt caa gga     384
Ile Val Asn Glu Lys Val Ser Ala Ala Ser Ile Ser Thr Cys Gln Gly
            115                 120                 125 cta cgg ggt tac atc agt caa gga gat gaa aag tat ttt atc gaa cct     432
Leu Arg Gly Tyr Ile Ser Gln Gly Asp Glu Lys Tyr Phe Ile Glu Pro
        130                 135                 140 ttg agc tcg gag aac ttg gat gaa cag gca cat gca ctc ttc aag gac     480
```

```
Leu Ser Ser Glu Asn Leu Asp Glu Gln Ala His Ala Leu Phe Lys Asp
145                 150                 155                 160 gac tcc aat gaa gac cag gag aag agc aac tgt ggt gtg gat gat gcg        528
Asp Ser Asn Glu Asp Gln Glu Lys Ser Asn Cys Gly Val Asp Asp Ala
                    165                 170                 175 cta tgg ctc caa ggg ctg cat cag gac gtg gcc ctc cct gcc acc agg        576
Leu Trp Leu Gln Gly Leu His Gln Asp Val Ala Leu Pro Ala Thr Arg
                180                 185                 190 ttg att aag ttg aat gat ggg atg gtt caa gaa cct aag aaa tac ata        624
Leu Ile Lys Leu Asn Asp Gly Met Val Gln Glu Pro Lys Lys Tyr Ile
            195                 200                 205 gaa tat tat gtg gtc ctg gat aat ggt gag ttt aag aaa tac aat aaa        672
Glu Tyr Tyr Val Val Leu Asp Asn Gly Glu Phe Lys Lys Tyr Asn Lys
        210                 215                 220 aat ctt gct gaa ata cga aag ata gtg ctt gag atg gcc aat tac atc        720
Asn Leu Ala Glu Ile Arg Lys Ile Val Leu Glu Met Ala Asn Tyr Ile
225                 230                 235                 240 aac atg ctt tac aat aag ctt gat gcc cac gtg gcc tta gtt gga gtg        768
Asn Met Leu Tyr Asn Lys Leu Asp Ala His Val Ala Leu Val Gly Val
                245                 250                 255 gaa atc tgg acc gat ggg gat aaa ata aag ata aca cca gat gcc aac        816
Glu Ile Trp Thr Asp Gly Asp Lys Ile Lys Ile Thr Pro Asp Ala Asn
                260                 265                 270 acc acc ctg gaa aac ttc tct aag tgg agg gga aat gat ctg cta aaa        864
Thr Thr Leu Glu Asn Phe Ser Lys Trp Arg Gly Asn Asp Leu Leu Lys
            275                 280                 285 cga aag cat cat gat att gcc cag cta atc tca tca aca gac ttt tct        912
Arg Lys His His Asp Ile Ala Gln Leu Ile Ser Ser Thr Asp Phe Ser
        290                 295                 300 gga tca aca gtg ggt cta gcc ttc atg tcg tcg atg tgt tca cct tac        960
Gly Ser Thr Val Gly Leu Ala Phe Met Ser Ser Met Cys Ser Pro Tyr
305                 310                 315                 320 cat tct gtt ggc att gtt cag gac cac agt aac tac cat ctt cga gtc       1008
His Ser Val Gly Ile Val Gln Asp His Ser Asn Tyr His Leu Arg Val
                325                 330                 335 gca gga aca atg gct cat gaa atg ggt cac aat ctt ggc atg att cat       1056
Ala Gly Thr Met Ala His Glu Met Gly His Asn Leu Gly Met Ile His
                340                 345                 350 gac tac ttg agc tgc aag tgt cca tct gaa gtc tgt gta atg gag cag       1104
Asp Tyr Leu Ser Cys Lys Cys Pro Ser Glu Val Cys Val Met Glu Gln
            355                 360                 365 tca cta agg ttc cat atg cct aca gac ttc agc tcc tgc agt cgt gtc       1152
Ser Leu Arg Phe His Met Pro Thr Asp Phe Ser Ser Cys Ser Arg Val
370                 375                 380 aat tac aaa cag ttt ctt gaa gaa aaa tta tcg cat tgc ctc ttt aat       1200
Asn Tyr Lys Gln Phe Leu Glu Glu Lys Leu Ser His Cys Leu Phe Asn
385                 390                 395                 400 agc cca ttg cca tca gat atc ata tcc acc cca gtc tgt ggg aac cag       1248
Ser Pro Leu Pro Ser Asp Ile Ile Ser Thr Pro Val Cys Gly Asn Gln
                405                 410                 415 ttg ttg gaa atg aat gag gac tgt gac tgt ggc aca ccc aag gag tgt       1296
Leu Leu Glu Met Asn Glu Asp Cys Asp Cys Gly Thr Pro Lys Glu Cys
                420                 425                 430 act aac aaa tgc tgt gat gca agg acc tgt aaa att aaa gca ggt ttc       1344
Thr Asn Lys Cys Cys Asp Ala Arg Thr Cys Lys Ile Lys Ala Gly Phe
            435                 440                 445 cag tgt gcc ctg ggg gaa tgt tgt gag aaa tgc caa ctt aaa aaa cct       1392
Gln Cys Ala Leu Gly Glu Cys Cys Glu Lys Cys Gln Leu Lys Lys Pro
        450                 455                 460
```

```
                                                       -continued
ggg gtt gtg tgc aga gca gca aaa gat gag tgt gat ctg cct gaa gtg              1440
Gly Val Val Cys Arg Ala Ala Lys Asp Glu Cys Asp Leu Pro Glu Val
465                 470                 475                 480 tgt gat ggt aaa tcc agc cac tgc cca ggt gac aga ttc aga gtc aat              1488
Cys Asp Gly Lys Ser Ser His Cys Pro Gly Asp Arg Phe Arg Val Asn
                485                 490                 495 ggc tcc cct tgc caa aat ggg cat ggt tac tgc ttg aag ggc aaa tgt              1536
Gly Ser Pro Cys Gln Asn Gly His Gly Tyr Cys Leu Lys Gly Lys Cys
            500                 505                 510 ccc acc ctg cag cag cag tgc atg gac atg tgg ggt cca gga acc aag              1584
Pro Thr Leu Gln Gln Gln Cys Met Asp Met Trp Gly Pro Gly Thr Lys
        515                 520                 525 gtt gca aat aca tca tgt tac aag cag aat gaa ggt ggg aca aag tac              1632
Val Ala Asn Thr Ser Cys Tyr Lys Gln Asn Glu Gly Gly Thr Lys Tyr
    530                 535                 540 gga tac tgt cat gtg gag aat ggc aca cac atg ccc tgc aaa gca aaa              1680
Gly Tyr Cys His Val Glu Asn Gly Thr His Met Pro Cys Lys Ala Lys
545                 550                 555                 560 gat gcc atg tgt ggg aaa ttg ttc tgt gaa ggc gga tca ggt gat ttg              1728
Asp Ala Met Cys Gly Lys Leu Phe Cys Glu Gly Gly Ser Gly Asp Leu
                565                 570                 575 ccc tgg aaa gga ctt acc ata tct ttc ctg aca tgt aaa tta ttt gat              1776
Pro Trp Lys Gly Leu Thr Ile Ser Phe Leu Thr Cys Lys Leu Phe Asp
            580                 585                 590 cct gaa gac aca agt caa gga gta gac atg gtg gcc aat gga acc aag              1824
Pro Glu Asp Thr Ser Gln Gly Val Asp Met Val Ala Asn Gly Thr Lys
        595                 600                 605 tgt gga act aac aag gtg tgc att aat gct gag tgt gtg gac atg gag              1872
Cys Gly Thr Asn Lys Val Cys Ile Asn Ala Glu Cys Val Asp Met Glu
    610                 615                 620 aag act tac aag tca gcc aac tgc tcc tca aag tgc aag ggg cac gca              1920
Lys Thr Tyr Lys Ser Ala Asn Cys Ser Ser Lys Cys Lys Gly His Ala
625                 630                 635                 640 gtg tgt gac cat gag ctt cag tgt cag tgc aag gaa gga tgg gcc cct              1968
Val Cys Asp His Glu Leu Gln Cys Gln Cys Lys Glu Gly Trp Ala Pro
                645                 650                 655 cct gac tgc gag aat tca gcc aca gtc ttc cac ttc tcc atc gtg gtt              2016
Pro Asp Cys Glu Asn Ser Ala Thr Val Phe His Phe Ser Ile Val Val
            660                 665                 670 ggc gtg ctt ttc ccc cta gca gtc ata ttt gtg gtg gtt gct ata gtg              2064
Gly Val Leu Phe Pro Leu Ala Val Ile Phe Val Val Val Ala Ile Val
        675                 680                 685 atc cag cgc caa agt gcc aga agg aag cag agg aga gtt cag agg cta              2112
Ile Gln Arg Gln Ser Ala Arg Arg Lys Gln Arg Arg Val Gln Arg Leu
    690                 695                 700 cca tcc acc aag gat gcc aag cta cac aat cag aag tgt aga ccc caa              2160
Pro Ser Thr Lys Asp Ala Lys Leu His Asn Gln Lys Cys Arg Pro Gln
705                 710                 715                 720 aag gtg aag gat gtt caa ccc cag gag atg agt cag atg aaa aag ctc              2208
Lys Val Lys Asp Val Gln Pro Gln Glu Met Ser Gln Met Lys Lys Leu
                725                 730                 735 cat gtg tct gat ctg ccc tct gaa gag ccg gag cct cca cct gat gtc              2256
His Val Ser Asp Leu Pro Ser Glu Glu Pro Glu Pro Pro Pro Asp Val
            740                 745                 750 cta atc aca aag cca aat ttc cca cca cca cca att cct gtt tcc ttg              2304
Leu Ile Thr Lys Pro Asn Phe Pro Pro Pro Pro Ile Pro Val Ser Leu
        755                 760                 765 gac cca aat gca aaa gtc tga                                                  2325
Asp Pro Asn Ala Lys Val
    770
```

<210> SEQ ID NO 26
<211> LENGTH: 774
<212> TYPE: PRT
<213> ORGANISM: Mus musculus

<400> SEQUENCE: 26

```
Met Gln Gln Trp Ser Leu Leu Val Val Ser Phe Leu Leu Ser Pro Val
1               5                   10                  15

Pro Val Ser Ala Ile Lys Glu Leu Pro Lys Ala Lys Lys Tyr Glu Val
                20                  25                  30

Val Tyr Pro Ile Arg Leu His Pro Leu Arg Lys Arg Glu Thr Gln Glu
            35                  40                  45

Pro Glu Pro Lys Glu Thr Phe Glu Thr Glu Leu Arg Tyr Lys Met Thr
        50                  55                  60

Val Asn Gly Lys Val Ala Val Leu Tyr Leu Lys Lys Asn Asn Lys Leu
65                  70                  75                  80

Leu Ala Pro Asp Tyr Ser Glu Thr Tyr Tyr Asn Ser Ser Gly Asn Lys
                85                  90                  95

Val Thr Thr Ser Pro Gln Ile Met Asp Ser Cys Tyr Tyr Gln Gly His
            100                 105                 110

Ile Val Asn Glu Lys Val Ser Ala Ala Ser Ile Ser Thr Cys Gln Gly
        115                 120                 125

Leu Arg Gly Tyr Ile Ser Gln Gly Asp Glu Lys Tyr Phe Ile Glu Pro
    130                 135                 140

Leu Ser Ser Glu Asn Leu Asp Glu Gln Ala His Ala Leu Phe Lys Asp
145                 150                 155                 160

Asp Ser Asn Glu Asp Gln Glu Lys Ser Asn Cys Gly Val Asp Asp Ala
                165                 170                 175

Leu Trp Leu Gln Gly Leu His Gln Asp Val Ala Leu Pro Ala Thr Arg
            180                 185                 190

Leu Ile Lys Leu Asn Asp Gly Met Val Gln Glu Pro Lys Lys Tyr Ile
        195                 200                 205

Glu Tyr Tyr Val Val Leu Asp Asn Gly Glu Phe Lys Lys Tyr Asn Lys
    210                 215                 220

Asn Leu Ala Glu Ile Arg Lys Ile Val Leu Glu Met Ala Asn Tyr Ile
225                 230                 235                 240

Asn Met Leu Tyr Asn Lys Leu Asp Ala His Val Ala Leu Val Gly Val
                245                 250                 255

Glu Ile Trp Thr Asp Gly Asp Lys Ile Lys Ile Thr Pro Asp Ala Asn
            260                 265                 270

Thr Thr Leu Glu Asn Phe Ser Lys Trp Arg Gly Asn Asp Leu Leu Lys
        275                 280                 285

Arg Lys His His Asp Ile Ala Gln Leu Ile Ser Ser Thr Asp Phe Ser
    290                 295                 300

Gly Ser Thr Val Gly Leu Ala Phe Met Ser Ser Met Cys Ser Pro Tyr
305                 310                 315                 320

His Ser Val Gly Ile Val Gln Asp His Ser Asn Tyr His Leu Arg Val
                325                 330                 335

Ala Gly Thr Met Ala His Glu Met Gly His Asn Leu Gly Met Ile His
            340                 345                 350

Asp Tyr Leu Ser Cys Lys Cys Pro Ser Glu Val Cys Val Met Glu Gln
        355                 360                 365

Ser Leu Arg Phe His Met Pro Thr Asp Phe Ser Ser Cys Ser Arg Val
```

```
                370             375             380
Asn Tyr Lys Gln Phe Leu Glu Glu Lys Leu Ser His Cys Leu Phe Asn
385                 390                 395                 400

Ser Pro Leu Pro Ser Asp Ile Ile Ser Thr Pro Val Cys Gly Asn Gln
                405                 410                 415

Leu Leu Glu Met Asn Glu Asp Cys Asp Cys Gly Thr Pro Lys Glu Cys
                420                 425                 430

Thr Asn Lys Cys Cys Asp Ala Arg Thr Cys Lys Ile Lys Ala Gly Phe
            435                 440                 445

Gln Cys Ala Leu Gly Glu Cys Cys Glu Lys Cys Gln Leu Lys Lys Pro
            450                 455                 460

Gly Val Val Cys Arg Ala Ala Lys Asp Glu Cys Asp Leu Pro Glu Val
465                 470                 475                 480

Cys Asp Gly Lys Ser Ser His Cys Pro Gly Asp Arg Phe Arg Val Asn
                485                 490                 495

Gly Ser Pro Cys Gln Asn Gly His Gly Tyr Cys Leu Lys Gly Lys Cys
                500                 505                 510

Pro Thr Leu Gln Gln Gln Cys Met Asp Met Trp Gly Pro Gly Thr Lys
                515                 520                 525

Val Ala Asn Thr Ser Cys Tyr Lys Gln Asn Glu Gly Gly Thr Lys Tyr
530                 535                 540

Gly Tyr Cys His Val Glu Asn Gly Thr His Met Pro Cys Lys Ala Lys
545                 550                 555                 560

Asp Ala Met Cys Gly Lys Leu Phe Cys Glu Gly Gly Ser Gly Asp Leu
                565                 570                 575

Pro Trp Lys Gly Leu Thr Ile Ser Phe Leu Thr Cys Lys Leu Phe Asp
                580                 585                 590

Pro Glu Asp Thr Ser Gln Gly Val Asp Met Val Ala Asn Gly Thr Lys
                595                 600                 605

Cys Gly Thr Asn Lys Val Cys Ile Asn Ala Glu Cys Val Asp Met Glu
            610                 615                 620

Lys Thr Tyr Lys Ser Ala Asn Cys Ser Ser Lys Cys Lys Gly His Ala
625                 630                 635                 640

Val Cys Asp His Glu Leu Gln Cys Gln Cys Lys Glu Gly Trp Ala Pro
                645                 650                 655

Pro Asp Cys Glu Asn Ser Ala Thr Val Phe His Phe Ser Ile Val Val
                660                 665                 670

Gly Val Leu Phe Pro Leu Ala Val Ile Phe Val Val Ala Ile Val
                675                 680                 685

Ile Gln Arg Gln Ser Ala Arg Arg Lys Gln Arg Val Gln Arg Leu
690                 695                 700

Pro Ser Thr Lys Asp Ala Lys Leu His Asn Gln Lys Cys Arg Pro Gln
705                 710                 715                 720

Lys Val Lys Asp Val Gln Pro Gln Glu Met Ser Gln Met Lys Lys Leu
                725                 730                 735

His Val Ser Asp Leu Pro Ser Glu Glu Pro Glu Pro Pro Asp Val
                740                 745                 750

Leu Ile Thr Lys Pro Asn Phe Pro Pro Pro Ile Pro Val Ser Leu
                755                 760                 765

Asp Pro Asn Ala Lys Val
770

<210> SEQ ID NO 27
```

```
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 27

Glu Gly Gly Ser Lys Tyr Gly Tyr
1               5
```

ANTI-HUMAN MEMBRANE-TYPE ADAM28 ANTIBODY

CROSS-REFERENCE TO RELATED APPLICATIONS

This patent application is the U.S. national phase of International Patent Application No. PCT/JP2016/056810, filed on Mar. 4, 2016, which claims the benefit of Japanese Patent Application No. 2015-045244, filed on Mar. 6, 2015, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 76,584 bytes ASCII (Text) file named "730683SequenceListing.txt," created Sep. 5, 2017.

TECHNICAL FIELD

The present invention relates to an anti-human membrane-anchored form ADAM28 antibody, and use thereof.

BACKGROUND ART

A missile therapy including binding an antitumor compound such as chemotherapeutic agent, radioisotope, toxin and the like to a monoclonal antibody against an antigen specifically expressed in cancer cells, and selectively delivering same to the target has entered a practical stage. In the missile therapy, side effects of an antitumor compound are expected to be reduced, since it is possible to selectively attack cancer tissues while suppressing uptake of the antitumor compound by normal cells. As an antibody used in the missile therapy targeting cancer, KADCYLA (Trastuzumab Emtansine) and the like are known. Since there are a variety of cancer cells, it is desirable to have many variations of antibodies useful for the missile therapy to be able to deal with the antigen expression pattern of target cancer cells.

ADAM proteins (ADAMs: a disintegrin and metalloproteinases) are multifunctional proteins involved in the ectodomain shedding of transmembrane proteins, cell adhesion and infiltration (non-patent documents 1, 2). The human genome contains 25 ADAMs including four pseudogenes and 21 kinds of ADAMS are composed of 13 kinds of proteolytic ADAMs that exhibit proteolytic activity and 8 kinds of non-proteolytic ADAMs (non-patent documents 1, 3). Proteolytic ADAMs share the metalloproteinase domain of matrix metalloproteinases (MMPs), and a typical proteolytic ADAM protein comprises propeptide, metalloproteinase, disintegrin-like, cysteine-rich, epidermal growth factor-like, transmembranes and cytoplasmic domains (non-patent documents 3-9). Many proteolytic ADAMs, including ADAM8, ADAM9, ADAM12, ADAM15, ADAM17, ADAM19 and ADAM28 are overexpressed in human cancers and are associated with tumor growth and progression (non-patent documents 5, 9). The present inventors' previous studies have indicated that ADAM28 (also known as ADAM metallopeptidase domain 28), which has two alternative isoforms, including a prototype membrane-anchored form (ADAM28m) and a short secreted form (ADAM28s) (non-patent documents 5, 10, 11), is abundantly expressed in human non-small cell lung carcinoma and breast carcinoma (non-patent documents 12, 13). By in situ hybridization and immunohistochemistry, the present inventors have demonstrated that ADAM28 is expressed predominantly in carcinoma cells contained in carcinoma tissues and that ADAM28 mRNA expression levels are associated with the cellular proliferation of breast cancer (non-patent document 13) and with both proliferation and infiltration of cancer cells in non-small cell lung cancer (non-patent document 12). In a parallel study, the present inventors showed that serum ADAM28 levels in non-small cell lung cancer patients substantially increase with the progression of tumor, lymph node metastasis, and cancer recurrence (non-patent document 14). These data imply that ADAM28 is involved in cell proliferation and metastasis particularly in human cancer. The present inventors have demonstrated that ADAM28 contributes to cancer cell proliferation through increased bioavailability of insulin-like growth factor-I (IGF-I) by selective digestion of IGF-binding protein-3 (IGFBP-3) in IGF-I/IGFBP-3 complex (non-patent document 13), and to angiogenesis by digestion of connective tissue growth factor in breast cancer (non-patent document 15).

The present inventors obtained an anti-human ADAM28 antibody showing a superior proliferation suppressive effect and a cancer metastasis inhibitory effect against cancer cells (patent document 1).

DOCUMENT LIST

Patent Document

[patent document 1] WO 2014/073292 A1

Non-Patent Documents

[non-patent document 1] Mol Aspects Med. 2008; 29 (5): 258-289
[non-patent document 2] Semin Cell Dev Biol. 2009; 20 (2): 138-145
[non-patent document 3] Pathol Int. 2010; 60 (7): 477-496
[non-patent document 4] Genes Dev. 2003; 17 (1): 7-30
[non-patent document 5] Cancer Sci. 2007; 98 (5): 621-628
[non-patent document 6] Nat Rev Mol Cell Biol. 2005; 6 (1): 32-43
[non-patent document 7] Kelley's Textbook of Rheumatology. 8th ed. Philadelphia, Pa.: Elsevier Saunders; 2009: 115-134
[non-patent document 8] Curr Opin Cell Biol. 2003; 15 (5): 598-606
[non-patent document 9] Nat Rev Cancer. 2008; 8 (12): 929-941
[non-patent document 10] J Biol Chem. 1999; 274 (41): 29251-29259
[non-patent document 11] Curr Pharm Des. 2009; 15 (20): 2349-2358
[non-patent document 12] Int J Cancer. 2006; 118 (2): 263-273
[non-patent document 13] Cancer Res. 2006; 66 (20): 9913-9920
[non-patent document 14] Int J Cancer. 2010; 127 (8): 1844-1856
[non-patent document 15] Biochem Biophys Res Commun. 2010; 402 (4): 651-657

SUMMARY OF THE INVENTION

Problems to be Solved by the Invention

The present inventors studied usefulness of the previously-obtained anti-ADAM28 antibody (patent document 1)

in the missile therapy. As a result, it was clarified that this anti-human ADAM28 antibody binds to a cancer cell that expresses membrane-anchored form ADAM28 (ADAM28m) and can be used in the missile therapy as a carrier that delivers an antitumor compound to cancer cells, whereas cancer cells that express membrane-anchored form ADAM28 also simultaneously express secreted form ADAM28 (ADAM28s) in many cases, and the secreted form ADAM28 binds to anti-ADAM28 antibody competitively with membrane-anchored form ADAM28 and may inhibit binding of anti-ADAM28 antibody to the cancer cells. Binding of a conjugate containing an anti-ADAM28 antibody and an antitumor compound to secreted form ADAM28 in the blood flow not only makes it impossible for the conjugate to deliver the antitumor compound to the target cancer cells, but also creates a risk of inducing side effects since the antitumor compound is incorporated into normal cells.

An object of the present invention is to provide an anti-ADAM28 antibody useful for the missile therapy of cancer cells that express membrane-anchored form ADAM28.

Means of Solving the Problems

The present inventors have conducted intensive studies in an attempt to solve the aforementioned problems and successfully established a monoclonal antibody which specifically binds to human membrane-anchored form ADAM28, and does not bind to human secreted form ADAM28 by immunizing a mouse with a recombinant protein of a domain specific to human membrane-anchored form ADAM28, establishing hybridoma from the immunized lymphocyte, and selecting a clone that specifically reacts with the immunizing antigen. The obtained monoclonal antibody has high binding activity to human membrane-anchored form ADAM28, and was useful as a delivery vehicle in the missile therapy targeting cancer cells that express human membrane-anchored form ADAM28. The present inventors have further studied based on the above findings, and completed the present invention.

That is, the present invention relates to the following.

[1] An antibody having an activity to specifically bind to human membrane-anchored form ADAM28 at an epitope in a region of the 524th-659th amino acids in the amino acid sequence shown in SEQ ID NO: 2.

[2] The antibody of [1], wherein the epitope is in a region of the 536th-543rd amino acids in the amino acid sequence shown in SEQ ID NO: 2.

[3] The antibody of [1] or [2], which does not have an activity to bind to human secreted form ADAM28.

[4] The antibody of any of [1]-[3], comprising a light chain variable region and a heavy chain variable region, wherein (1) the light chain variable region comprises CDR1 comprising the amino acid sequence shown in SEQ ID NO: 5, CDR2 comprising the amino acid sequence shown in SEQ ID NO: 6 and CDR3 comprising the amino acid sequence shown in SEQ ID NO: 7, and the heavy chain variable region comprises CDR1 comprising the amino acid sequence shown in SEQ ID NO: 8, CDR2 comprising the amino acid sequence shown in SEQ ID NO: 9 and CDR3 comprising the amino acid sequence shown in SEQ ID NO: 10; or (2) the light chain variable region comprises CDR1 comprising the amino acid sequence shown in SEQ ID NO: 5, CDR2 comprising the amino acid sequence shown in SEQ ID NO: 6 and CDR3 comprising the amino acid sequence shown in SEQ ID NO: 7, and the heavy chain variable region comprises CDR1 comprising the amino acid sequence shown in SEQ ID NO: 8, CDR2 comprising the amino acid sequence shown in SEQ ID NO: 9 and CDR3 comprising the amino acid sequence shown in SEQ ID NO: 10, except that 1 to 3 amino acids are substituted, deleted, inserted, and/or added in at least one amino acid sequence selected from the group consisting of the amino acid sequences shown in SEQ ID NOs: 5, 6 and 7, and/or 1 to 3 amino acids are substituted, deleted, inserted, and/or added in at least one amino acid sequence selected from the group consisting of the amino acid sequences shown in SEQ ID NOs: 8, 9 and 10.

[5] The antibody of [4], wherein the light chain variable region comprises the amino acid sequence shown in SEQ ID NO: 11, and the heavy chain variable region comprises the amino acid sequence shown in SEQ ID NO: 12.

[6] A pharmaceutical composition comprising the antibody of any of [1]-[5].

[7] A drug delivery vehicle for delivering a drug to a cell or tissue that expresses a human membrane-anchored form ADAM28, which comprises the antibody of any of [1]-[5].

[8] The drug delivery vehicle of [7], wherein the cell or tissue further expresses human secreted form ADAM28.

[9] The drug delivery vehicle of [7] or [8], wherein the cell or tissue is a cancer cell or cancer tissue.

[10] A composition comprising an immune complex comprising a drug and the antibody of any of [1]-[5], for delivering the drug to a cell or tissue expressing human membrane-anchored form ADAM28.

[11] The composition of [10], wherein the cell or tissue further expresses human secreted form ADAM28.

[12] The composition of [10] or [11], wherein the cell or tissue is a cancer cell or cancer tissue.

[13] A method of delivering a drug to a cell or tissue expressing human membrane-anchored form ADAM28 in human, comprising administering an immune complex comprising the drug and the antibody of any of [1]-[5] to a human.

[14] The antibody of any of [1]-[5] for use for mediating deliver of a drug to a cell or tissue expressing human membrane-anchored form ADAM28.

[15] Use of the antibody of any of [1]-[5], for the production of a drug delivery vehicle for delivering a drug to a cell or tissue expressing human membrane-anchored form ADAM28.

[16] A polynucleotide encoding the antibody of any of [1]-[5].

[17] A vector comprising the polynucleotide of [16].

[18] A transformant comprising the vector of [17].

Effect of the Invention

According to the present invention, an anti-ADAM28 antibody which specifically binds to human membrane-anchored form ADAM28, and is useful for the missile therapy of cancer cells that express membrane-anchored form ADAM28, is provided.

BRIEF DESCRIPTION OF THE DRAWINGS

FIG. 4 shows comparison of reactivity of 2B6D10 antibody with human membrane-anchored form ADAM28 and mouse membrane-anchored form ADAM28 by ELISA.

DESCRIPTION OF EMBODIMENTS

Figure 1:
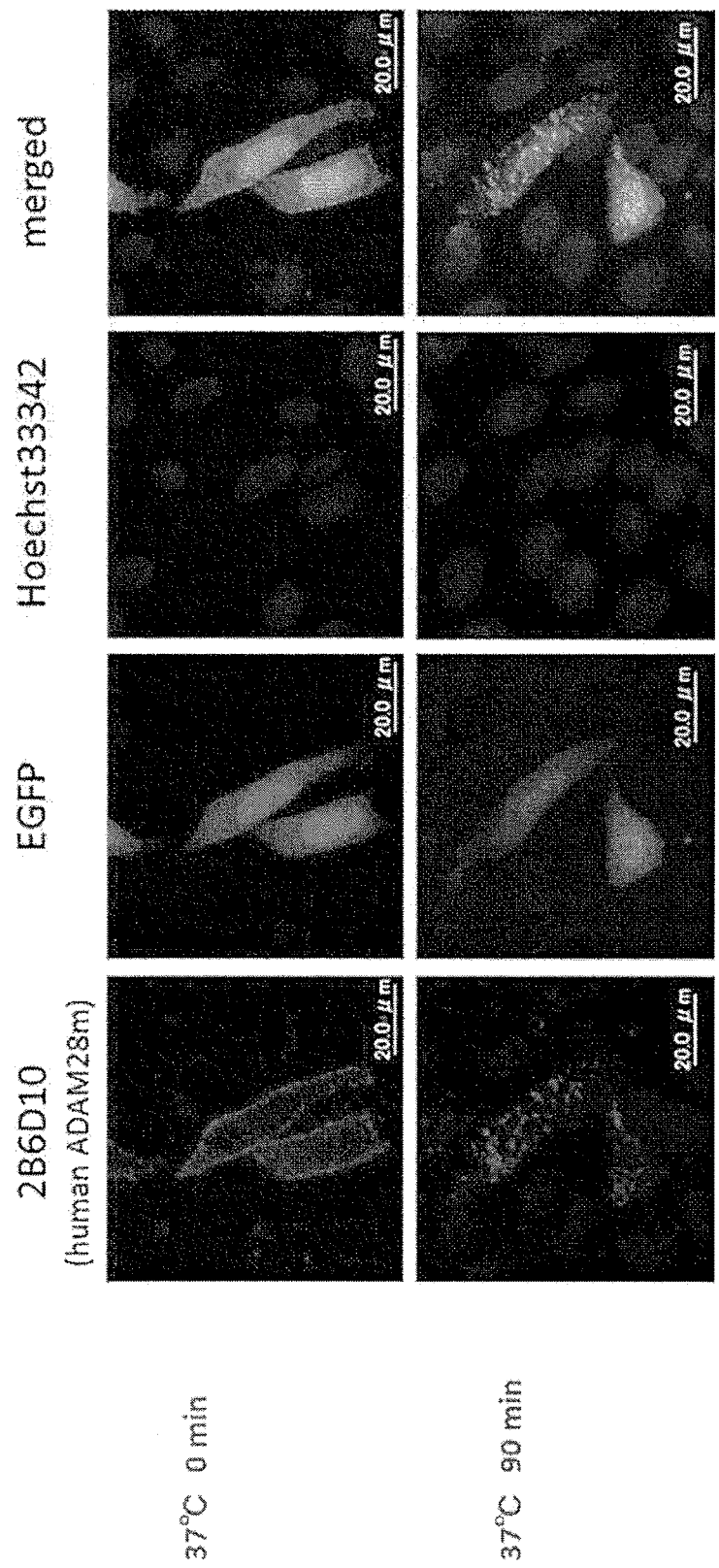
FIG. 1 shows a 2B6D10 antibody-stained image of CHO-K1 cells, transfected with human membrane-anchored form ADAM28.

The present invention provides an antibody having an activity to specifically bind to human membrane-anchored form ADAM28.

ADAM28 is a known protein, and the amino acid sequence thereof and the cDNA sequence thereof are also known. ADAM28 includes two kinds of a membrane form (ADAM28m) and a secreted form (ADAM28s). A representative amino acid sequence of human membrane-anchored form ADAM28 is shown in SEQ ID NO: 2, a representative cDNA sequence of human membrane-anchored form ADAM28 is shown in SEQ ID NO: 1, a representative amino acid sequence of human secreted form ADAM28 is shown in SEQ ID NO: 4, and a representative cDNA sequence of human secreted form ADAM28 is shown in SEQ ID NO: 3. A representative amino acid sequence of human membrane-anchored form ADAM28 (mature form) is shown in SEQ ID NO: 22, a representative cDNA sequence of human membrane-anchored form ADAM28 (mature form) is shown in SEQ ID NO: 21, a representative amino acid sequence of human secreted form ADAM28 (mature form) is shown in SEQ ID NO: 24, and a representative cDNA sequence of human secreted form ADAM28 (mature form) is shown in SEQ ID NO: 23. SEQ ID NO: 22 corresponds to the 199th-775th amino acids of SEQ ID NO: 2.

The "human membrane-anchored form ADAM28" means that the amino acid sequence or nucleotide sequence of membrane-anchored form ADAM28 has the same or substantially the same amino acid sequence or nucleotide sequence as the amino acid sequence or nucleotide sequence of membrane-anchored form ADAM28 naturally expressed in human. Being "substantially the same" means that the amino acid sequence or nucleotide sequence of interest has not less than 70% (preferably not less than 80%, more preferably not less than 90%, more preferably not less than 95%, most preferably not less than 99%), identity with the amino acid sequence or nucleotide sequence of membrane-anchored form ADAM28 naturally expressed in human, and has the function of human membrane-anchored form ADAM28. Terms for biological species other than human, proteins and genes other than membrane-anchored form ADAM28, and fragments thereof are also interpreted in the same manner.

The "specific binding" of an antibody to antigen X means that the binding affinity of the antibody to antigen X in an antigen-antibody reaction is higher than the binding affinity to a non-specific antigen (e.g., bovine serum albumin (BSA)).

In one embodiment, the $K_D$ value of the binding affinity of the antibody of the present invention to human membrane-anchored form ADAM28 in an antigen-antibody reaction is not more than $1\times10^{-7}$ M (e.g., not more than $1\times10^{-8}$ M, not more than $1\times10^{-9}$ M, not more than $1\times10^{-10}$ M, not more than $1\times10^{-11}$ M).

The antibody of the present invention specifically binds to human membrane-anchored form ADAM28 at an epitope in a region of the 524th-659th amino acids in the amino acid sequence shown in SEQ ID NO: 2. The antibody of the present invention is preferably specifically binds to human membrane-anchored form ADAM28 at an epitope in a region of the 536th-543rd amino acids in the amino acid sequence shown in SEQ ID NO: 2. The region of the 524th-659th amino acids in the amino acid sequence shown in SEQ ID NO: 2, and the region of the 536th-543rd amino acids in the amino acid sequence shown in SEQ ID NO: 2 exist in human membrane-anchored form ADAM28, but not exist in human secreted form ADAM28. Accordingly, the antibody of the present invention does not have an activity to bind to human secreted form ADAM28. In one embodiment, the $K_D$ value of the binding affinity of the antibody of the present invention to human secreted form ADAM28 in an antigen-antibody reaction is not less than $1\times10^{-5}$ M (e.g., not less than $1\times10^{-4}$ M, not less than $1\times10^{-3}$ M, not less than $1\times10^{-2}$ M, not less than $1\times10^{-1}$ M).

The antibody of the present invention optionally has an activity to specifically bind to mouse membrane-anchored form ADAM28. Having cross-reactivity with mouse membrane-anchored form ADAM28, the experimental results relating to the pharmacological effects and safety of the antibody of the present invention by using mouse are easily extrapolated into human. The region of the 524th-659th amino acids in the amino acid sequences shown in SEQ ID NO: 2 is highly preserved between human ADAM28 and mouse ADAM28. Therefore, those of ordinary skill in the art can obtain an antibody having cross-reactivity with mouse membrane-anchored form ADAM28 from the antibodies of the present invention without undue experimentation. When the antibody of the present invention has cross-reactivity with mouse membrane-anchored form ADAM28, the $K_D$ value of the binding affinity of the antibody of the present invention to mouse membrane-anchored form ADAM28 in an antigen-antibody reaction is not more than $1\times10^{-7}$ M (e.g., not more than $1\times10^{-8}$ M, not more than $1\times10^{-9}$ M, not more than $1\times10^{-10}$ M, not more than $1\times10^{-11}$ M). A representative amino acid sequence of mouse membrane-anchored form ADAM28 is shown in SEQ ID NO: 26, and a representative cDNA sequence of mouse membrane-anchored form ADAM28 is shown in SEQ ID NO: 25.

In one embodiment, when the antibody of the present invention has cross-reactivity with mouse membrane-anchored form ADAM28, the $K_D$ value of the binding affinity of the antibody of the present invention to human membrane-anchored form ADAM28 in an antigen-antibody reaction is not more than $1\times10^{-7}$ M (e.g., not more than $1\times10^{-8}$ M, not more than $1\times10^{-9}$ M, not more than $1\times10^{-10}$ M, not more than $1\times10^{-11}$ M), and the $K_D$ value of the binding affinity of the antibody of the present invention to mouse membrane-anchored form ADAM28 in an antigen-antibody reaction is not more than $1\times10^{-7}$ M (e.g., not more than $1\times10^{-8}$ M, not more than $1\times10^{-9}$ M, not more than $1\times10^{-10}$ M, not more than $1\times10^{-11}$ M).

The $K_D$ value of the binding affinity of an antibody to an antigen (e.g., human membrane-anchored form ADAM28, mouse membrane-anchored form ADAM28) in an antigen-antibody reaction can be obtained by, for example, measuring the Ka value and the Kd value by surface plasmon resonance with BIAcore 3000 (GE Healthcare Life Sciences), and calculating from the obtained Ka value and Kd value. In the measurement of the $K_D$ value, not only the full-length of the antigen but also an antigen fragment containing the epitope, a fusion protein of other protein and the antigen or a fragment thereof containing the epitope may also be used. For example, when $K_D$ values of an antibody against human membrane-anchored form ADAM28 and mouse membrane-anchored form ADAM28 are measured, a fusion protein (MBP-human ADAM28m 524-659) in which a region of 524-659 of human membrane-anchored form ADAM28 (SEQ ID NO: 2) is fused to the C-terminal of MBP, and a fusion protein (MBP-mouse ADAM28m 527-622) in which a region of 527-622 of mouse membrane-anchored form ADAM28 (SEQ ID NO: 26) is fused to the C-terminal of MBP are each immobilized on CM5 sensor chip (GE Healthcare Life Sciences, Buckinghamshire, UK) by amine coupling, an evaluation target antibody is injected to a flow cell by using BIAcore 3000, Ka and Kd values are measured, $N_D$ values are calculated from the obtained Ka and Kd values, and these are taken as $N_D$ values of the evaluation target antibody against human membrane-anchored form ADAM28 and mouse membrane-anchored form ADAM28.

A region of the 536th-543rd amino acids in the amino acid sequence shown in SEQ ID NO: 2 corresponds to a region of the 539th 546th amino acids of mouse membrane-anchored form ADAM28 (SEQ ID NO: 26). In this region, all amino acids are identical between human membrane-anchored form ADAM28 and mouse membrane-anchored form ADAM28 except conservative substitution of serine (the 539th amino acid of human membrane-anchored form ADAM28 (SEQ ID NO: 2)) with threonine (the 542nd amino acid of mouse membrane-anchored form ADAM28 (SEQ ID NO: 26)). Therefore, an antibody having an activity to specifically bind to human membrane-anchored form ADAM28 at an epitope in the region of the 536th-543rd amino acids in the amino acid sequence shown in SEQ ID NO: 2 may have cross-reactivity with mouse membrane-anchored form ADAM28.

In the present specification, the "antibody" is used as one encompassing a full-length antibody and any antigen-binding fragment (i.e., "antigen-binding portion") thereof or a single chain thereof. The "antibody" refers to a glycoprotein containing at least two heavy chains (H) and two light chains (L), which are linked by a disulfide bond, or an antigen-binding portion thereof. Each heavy chain is constituted by a heavy chain variable region (to be abbreviated as $V_H$ herein) and a heavy chain constant region. The heavy chain constant region is constituted by 3 domains of $C_H1$, $C_H2$ and $C_H3$. Each light chain is constituted by a light chain variable region (to be abbreviated as $V_L$ herein) and a light chain constant region. The light chain constant region is constituted by a single domain $C_L$. $V_H$ and $V_L$ regions are further subdivided into regions with higher variability called complementarity determining regions (CDRs), which contain more highly conservative regions called framework regions (FRs) scattered therein. Each $V_H$ and $V_L$ is constituted by 3 CDRs and 4 FRs, which are aligned in the following order, i.e., FR1, CDR1, FR2, CDR2, FR3, CDR3, FR4 from the amino terminal to the carboxy terminal. The variable regions of said heavy chain and light chain contain binding domains that interact with an antigen. The constant region of an antibody can mediate the binding of immunoglobulin to host tissues or factors, including various cells (e.g., effector cells) of the immune system and the first component (C1q) of the conventional complement system.

In the present specification, the "antigen-binding portion" of an antibody is used to refer to one or more fragments of an antibody retaining an ability to specifically bind to an antigen (e.g., human membrane-anchored form ADAM28). It has been clarified that the antigen binding function of an antibody is performed by this fragment of a full-length antibody. Examples of the binding fragment included in the term "antigen binding portion" of an antibody include (i) Fab fragment, a monovalent fragment constituted by $V_L$, $V_H$, $C_L$ and $C_{H1}$ domains, (ii) F(ab')$_2$ fragment, a divalent fragment containing two Fab fragments linked by disulfide bond in the hinge region, (iii) Fab' fragment, an inherent Fab having a hinge region portion (see FUNDAMENTAL IMMUNOLOGY, Paul ed., 3rd ed. 1993), (iv) Fd fragment constituted by $V_H$ and $C_{H1}$ domains, (v) Fv fragment constituted by $V_L$ and $V_H$ domains in a single arm of an antibody, (vi) dAb fragment constituted by $V_H$ domain (Ward et al., (1989) Nature 341:544-546), (vii) isolated complementarity determining region (CDR) and (viii) nanobody which is a heavy chain variable region containing single variable domain and two constant regions. While $V_L$ and $V_H$, which are the two domains of Fv fragment, are encoded by different genes, they can be linked by a synthetic linker to produce a single protein chain from them by recombinant techniques, wherein, in this chain, $V_L$ and $V_H$ regions pair with each other to form a monovalent molecule (known as a single chain Fv (scFv); see, for example, Bird et al. (1988) Science 242: 423-426; and Huston et al., (1988) Proc. Natl. Acad. Sci. USA 85: 5879-5883). Such single chain antibody is also encompassed in the "antigen-binding portion" of an antibody. Such antibody fragments are obtained by those of ordinary skill in the art by known conventional techniques, and screened for usefulness in the same manner as with unmodified antibody.

The antibody of the present invention may be any of polyclonal antibody (antiserum) and monoclonal antibody, and is preferably a monoclonal antibody. The "monoclonal antibody" refers to a preparation of an antibody molecule of a single molecule composition. The monoclonal antibody composition shows single binding-specificity and affinity for a particular epitope. The antibody may be any isotype of IgG, IgM, IgA, IgD or IgE and the like, and is preferably IgG or IgM.

Monoclonal antibody can be generated by a cell fusion method. For example, an isolated polypeptide containing a region of the 524th-659th amino acids or a region of the 536th-543rd amino acids in the amino acid sequence shown in SEQ ID NO: 2 is subcutaneously or intraperitoneally administered as an antigen to a mouse 2-4 times together with an adjuvant, spleen or lymph node is collected 3 days after the final administration, and lymphocytes (B-cells) are recovered. The lymphocytes (B-cells) and myeloma cells (e.g., NS-1, P3X63Ag8 and the like) are fused to give a hybridoma that produces a monoclonal antibody against the antigen. Cell fusion may be performed by a PEG method or voltage pulsation method. A hybridoma that produces a monoclonal antibody of interest can be selected by detecting an antibody that specifically binds to an antigen from the culture supernatant by a well-known EIA or RIA method and the like. The hybridoma that produces a monoclonal antibody can be cultured in vitro, or in vivo in mouse or rat, preferably in mouse ascites and the like, and an antibody can be obtained from a culture supernatant of hybridoma and ascites of an animal.

The antibody of the present invention may be a humanized antibody. In the present specification, moreover, "humanized antibody" is a monoclonal antibody produced by genetic engineering, which means a monoclonal antibody in which a complementarity-determining region in the variable region thereof is partly or entirely derived from the immunoglobulin of animal species other than human (e.g., mouse), and a framework region and a constant region thereof of the variable region are derived from human immunoglobulin. In other words, for example, it means a monoclonal antibody in which all regions other than a part or whole of the complementarity-determining region in the variable region of mouse monoclonal antibody is replaced by the corresponding regions of human immunoglobulin.

Humanized antibody can be produced according to a method known per se. For example, a recombinant humanized antibody derived from a mouse monoclonal antibody can be produced according to previous reports (e.g., National Publication of International Patent Application No. 4-506458 and JP-A-62-296890). In detail, at least one mouse H-chain CDR gene and at least one mouse L-chain CDR gene corresponding to the mouse H-chain CDR gene are isolated from a hybridoma that produces mouse monoclonal antibody, and a human H-chain gene encoding all regions other than human H-chain CDR corresponding to the aforementioned mouse H-chain CDR, and a human L-chain gene encoding all regions other than human L-chain CDR corresponding to mouse L-chain CDR are isolated from a human immunoglobulin gene. The isolated mouse H-chain CDR gene and the human H-chain gene are introduced into suitable expression vector to allow for expression, and similarly, the mouse L-chain CDR gene and the human L-chain gene are introduced into another suitable expression vector to allow for expression. Alternatively, the mouse H-chain CDR gene/human H-chain gene and the mouse L-chain CDR gene/human L-chain gene can also be introduced into the same expression vector to allow for expression. A host cell is transformed with the thus-produced expression vector to give humanized antibody-producing cells, and the cells are cultured to give a humanized antibody of interest from the culture supernatant.

The antibody of the present invention may be a human antibody. The "human antibody" refers to an antibody having variable regions derived from a human germline immunoglobulin sequence in both the framework and CDR regions. Furthermore, when an antibody contains a constant region, the constant region also derives from a human germline immunoglobulin sequence. In the present specification, the "human antibody" also encompasses even an embodiment including an amino acid residue not encoded by a human germline immunoglobulin sequence (e.g., mutation introduced by random or site-directed mutagenesis in vitro or somatic mutation in vivo).

Human antibody can be produced according to a method known per se. For example, human antibody can be produced by immunizing a transgenic animal produced by incorporating at least a human immunoglobulin gene into the gene locus of a mammal other than human such as mouse and the like, with an antigen, and treating the animal in the same manner as in the production method of the aforementioned polyclonal antibody or monoclonal antibody. For example, a transgenic mouse that produces human antibody can be produced according to previous reports (Nature Genetics, Vol. 15, p. 146-156, 1997; Nature Genetics, Vol. 7, p. 13-21, 1994; National Publication of International Patent Application No. 4-504365; WO 94/25585; Nature, Vol. 368, p. 856-859, 1994; and National Publication of International Patent Application No. 6-500233).

In the present specification, the human antibody encompasses a "reconstituted human antibody". The reconstituted human antibody refers to a modified antibody wherein at least one CDR contained in the first human donor antibody is used in the second human acceptor antibody, instead of CDR of the second human acceptor antibody. Preferably, all 6 CDRs are substituted. More preferably, the whole antigen binding region (e.g., Fv, Fab or F(ab')2) of the first human donor antibody is used instead of the corresponding region in the second human acceptor antibody. More preferably, the Fab region of the first human donor antibody is operably linked to an appropriate constant region of the second human acceptor antibody to form a full-length antibody.

The reconstituted human antibody can be produced by conventional gene recombinant techniques disclosed in, for example, EP125023, WO 96/02576 and the like. To be specific, for example, a DNA sequence designed to link a desired CDR in a donor human antibody and a desired framework region (FR) in an acceptor human antibody is synthesized by PCR method using, as primers, several oligonucleotides produced to have a region overlapping with the terminal regions of both CDR and FR (see the method described in WO 98/13388). The obtained DNA is linked to a DNA encoding a human antibody constant region or a human antibody constant region mutant, which is incorporated into an expression vector and the vector is introduced into a host to allow for production, whereby a reconstituted human antibody can be obtained (see EP125023, WO 96/02576).

In the present specification, moreover, the human antibody encompasses an "artificial human antibody". The artificial human antibody can be produced by conventional gene recombinant techniques disclosed in, for example, Rothe, C. et al. J. Mol. Biol. 2008; 376:1182-1200 and the like.

The antibody of the present invention also includes a fusion protein wherein the aforementioned antibody and other peptide or protein are fused. The production method of a fusion protein includes linking a polynucleotide encoding the antibody of the present invention and a polynucleotide encoding other peptide or polypeptide to match the frame, introducing same into an expression vector, and allowing expression thereof in a host, and techniques known to those of ordinary skill in the art can be used. As other peptide to be fused with the antibody of the present invention, known peptides such as FLAG (Hopp, T. P. et al., BioTechnology (1988) 6, 1204-1210), 6× His consisting of six His (histidine) residues, 10× His, human c-myc fragment, VSV-GP fragment, p18HIV fragment, T7-tag, HSV-tag, E-tag, SV40T antigen fragment, lck tag, α-tubulin fragment, B-tag, Protein C fragment and the like can be used. Examples of other polypeptide to be fused with the antibody of the present invention include GST (glutathione-S-transferase), HA (influenza hemagglutinin), immunoglobulin constant region, β-galactosidase, MBP (maltose binding protein) and the like. A commercially available polynucleotide encoding such peptide or polypeptide is fused with a polynucleotide encoding the antibody of the present invention, and a fusion polynucleotide prepared thereby is expressed, whereby a fusion polypeptide can be prepared.

The antibody of the present invention is preferably isolated or purified. Being "isolated or purified" means that an operation to remove components other than the component of interest has been applied to the state of natural presence. The purity of the isolated or purified antibody of the present invention (ratio of the weight of the antibody of the present invention to the total protein weight) is generally 50% or more, preferably 70% or more, more preferably 90% or more, most preferably 95% or more (e.g., substantially 100%).

As a preferable embodiment of the antibody of the present invention, the antibodies described in the following (1) and (2) can be mentioned:
(1) an antibody comprising a light chain variable region and a heavy chain variable region, wherein the light chain variable region comprises CDR1 comprising the amino acid sequence shown in SEQ ID NO: 5, CDR2 comprising the amino acid sequence shown in SEQ ID NO: 6 and CDR3 comprising the amino acid sequence shown in SEQ ID NO: 7, and the heavy chain variable region comprises CDR1 comprising the amino acid sequence shown in SEQ ID NO: 8, CDR2 comprising the amino acid sequence shown in SEQ ID NO: 9 and CDR3 comprising the amino acid sequence shown in SEQ ID NO: 10; and (2) an antibody comprising a light chain variable region and a heavy chain variable region, wherein the light chain variable region comprises CDR1 comprising the amino acid sequence shown in SEQ ID NO: 5, CDR2 comprising the amino acid sequence shown in SEQ ID NO: 6 and CDR3 comprising the amino acid sequence shown in SEQ ID NO: 7, and the heavy chain variable region comprises CDR1 comprising the amino acid sequence shown in SEQ ID NO: 8, CDR2 comprising the amino acid sequence shown in SEQ ID NO: 9 and CDR3 comprising the amino acid sequence shown in SEQ ID NO: 10 except that 1 to 3 amino acids are substituted, deleted, inserted, and/or added in at least one amino acid sequence selected from the group consisting of the amino acid sequences shown in SEQ ID NOs: 5, 6 and 7, and/or 1 to 3 amino acids are substituted, deleted, inserted, and/or added in at least one amino acid sequence selected from the group consisting of the amino acid sequences shown in SEQ ID NOs: 8, 9 and 10.

In the embodiment of (2), the number of amino acids to be substituted, deleted, inserted and/or added is not particularly limited as long as the antibody has an activity to specifically bind to human membrane-anchored form ADAM28 at an epitope in a region of the 524th-659th amino acids in the amino acid sequence shown in SEQ ID NO: 2 (preferably, epitope in a region of the 536th-543rd amino acids in the amino acid sequence shown in SEQ ID NO: 2). It is preferably within 2 amino acids, more preferably one amino acid, per one CDR sequence. While the number of CDR sequences in which amino acid(s) is(are) substituted, deleted, inserted and/or added is not particularly limited as long as the antibody has an activity to specifically bind to human membrane-anchored form ADAM28 at an epitope in a region of the 524th-659th amino acids in the amino acid sequence shown in SEQ ID NO: 2 (preferably, epitope in a region of the 536th-543rd amino acids in the amino acid sequence shown in SEQ ID NO: 2). It is preferably within 2, more preferably one, per one light chain variable region, and preferably within 2, more preferably 1, per one heavy chain variable region. The substitution, deletion, insertion and/or addition of amino acid may be performed in both the light chain variable region and the heavy chain variable region, or either one of them.

In the embodiments of (2), 1-3 (preferably 1 or 2, more preferably 1) amino acids are preferably substituted, deleted, inserted, and/or added only in the amino acid sequence of CDR3 in the light chain variable region.

Examples of the method for substituting one or plural amino acid residues with other desired amino acid include site-directed mutagenesis method (Hashimoto-Gotoh, T, Mizuno, T, Ogasahara, Y, and Nakagawa, M. (1995) An oligodeoxyribonucleotide-directed dual amber method for site-directed mutagenesis. Gene 152, 271-275; Zoller, M J, and Smith, M. (1983) Oligonucleotide-directed mutagenesis of DNA fragments cloned into M13 vectors. Methods Enzymol. 100, 468-500; Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456; Kramer W, and Fritz H J (1987) Oligonucleotide-directed construction of mutations via gapped duplex DNA Methods. Enzymol. 154, 350-367, Kunkel, T A (1985) Rapid and efficient site-specific mutagenesis without phenotypic selection. Proc Natl Acad Sci USA. 82, 488-492). Using these methods, desired amino acid in an antibody can be substituted by other amino acid of interest. Also, using the library technique such as framework shuffling (Mol Immunol. 2007 April; 44(11): 3049-60) and CDR repair (US2006/0122377) and the like, an amino acid in a framework or CDR can also be substituted by other appropriate amino acid.

In the antibody of the present invention, as a framework region (FR) of the antibody to be linked to a CDR, a framework which enables the CDR to form a good antigen binding site is selected. While FR to be used for the antibody of the present invention is not particularly limited and any FRs can be used, FR of a mouse or human antibody is preferably used. As the FR of a human antibody, one having a natural sequence may be used, or one or plural amino acids in the framework region having a natural sequence may be substituted, deleted, added and/or inserted and the like as necessary, so that CDR will form an appropriate antigen binding site. For example, a mutant FR sequence having desired properties can be selected by measuring and evaluating the binding activity of an antibody having FR with substituted amino acid to an antigen (Sato, K. et al., Cancer Res. (1993)53, 851-856).

The constant region used for the antibody of the present invention is not particularly limited, and any constant, region may be used. Preferable examples of the constant region used for the antibody of the present invention include constant regions of mouse or human antibody (constant regions derived from IgG1, IgG2, IgG3, IgG4, IgA, IgM and the like). For example, Cγ1, Cγ2, Cγ3, Cγ4, Cμ, Cδ, Cα1, Cα2, Cε can be used in H-chain, and Cκ, Cλ can be used in L-chain.

In one embodiment, in the antibody of (1), kappa constant region of mouse antibody is used as the light chain, and IgG2a constant region of mouse antibody is used as the heavy chain.

Preferable antibody of the present invention includes the following:

(1') An antibody comprising a light chain variable region and a heavy chain variable region, wherein the light chain variable region comprises the amino acid sequence shown in SEQ ID NO: 11 and the heavy chain variable region comprises the amino acid sequence shown in SEQ ID NO: 12.

The antibody of the above-mentioned (1') corresponds to a preferable embodiment of the antibody of the above-mentioned (1).

The present invention provides a polynucleotide containing a nucleotide sequence encoding the above-mentioned antibody of the present invention. The polynucleotide may be a DNA or RNA, or a DNA/RNA chimera. The polynucleotide may be double stranded or single stranded. When the polynucleotide is double stranded, it may be a double stranded DNA, a double stranded RNA or a DNA:RNA hybrid.

The polynucleotide of the present invention encompasses a polynucleotide containing a nucleotide sequence encoding both the heavy chain variable region and the light chain variable region of the antibody of the present invention, and a combination of a polynucleotide containing a nucleotide sequence encoding the heavy chain variable region of the antibody of the present invention and a polynucleotide containing a nucleotide sequence encoding the light chain variable region of the antibody of the present invention.

The polynucleotide of the present invention can be easily produced based on the information of the amino acid sequence of the antibody of the present invention, known sequence information and sequence information described in the Sequence Listing in the present specification, and by utilizing known gene recombination techniques. For example, suitable primers are designed based on the sequence information, a DNA encoding the elements constituting the antibody of the present invention is amplified by the PCR reaction, DNA fragments are ligated by appropriate enzymes such as ligase and the like, whereby the polynucleotide of the present invention can be produced. Alternatively, a polynucleotide encoding each element may be synthesized by a polynucleotide synthesizer, based on the information of the amino acid sequence of the antibody of the present invention.

The obtained polynucleotide encoding the antibody of the present invention may be, depending on the object, directly used, or used after digestion with a restriction enzyme when desired, or addition of a linker. The polynucleotide may have ATG as a translation initiation codon on the 5' terminal side, and may have TAA, TGA or TAG as a translation stop codon on the 3' terminal side. These translation initiation codon and translation stop codon can be added using a suitable synthesized DNA adapter.

The polynucleotide of the present invention is preferably isolated or purified. The isolated or purified polynucleotide of the present invention has a purity (ratio of the weight of the polynucleotide of the present invention to the total polynucleotide weight) of generally 50% or more, preferably 70% or more, more preferably 90% or more, most preferably 95% or more (e.g., substantially 100%).

The present invention provides a vector comprising the above-mentioned polynucleotide of the present invention. The vector of the present invention encompasses a vector comprising a polynucleotide comprising a nucleotide sequence encoding both the heavy chain variable region and the light chain variable region of the antibody of the present invention, and a combination of a vector comprising a polynucleotide comprising a nucleotide sequence encoding the heavy chain variable region of the antibody of the present invention and a vector comprising a polynucleotide comprising a nucleotide sequence encoding the light chain variable region of the antibody of the present invention. The vector is preferably isolated or purified. Examples of the vector include expression vector, cloning vector and the like, which can be selected according to the object. Preferably, the vector is an expression vector. The expression vector can express the antibody of the present invention. The expression vector can be produced by operably linking the polynucleotide of the present invention to the downstream of a promoter in a suitable expression vector. The kind of the vector includes, for example, plasmid vector, virus vector and the like, which can be appropriately selected according to the host to be used.

As the host, the genus Escherichia (Escherichia coli etc.), the genus Bacillus (Bacillus subtilis etc.), yeast (Saccharomyces cerevisiae etc.), insect cell (established cell line derived from larva of Mamestra brassicae (Spodoptera frugiperda cell; Sf cell) etc.), insect (larva of Bombyx mori etc.), mammalian cells (rat nerve cell, monkey cell (COS-7 etc.), Chinese hamster cell (CHO cell etc.) etc.) and the like are used.

Examples of the mammal include, but are not limited to, experiment animals such as rodents such as mouse, rat, hamster and guinea pig and the like, rabbit and the like, domestic animals such as swine, bovine, goat, horse, sheep, mink and the like, companion animals such as dog, cat and the like, primates such as human, monkey, Macaca fascicularis, Macaca mulatta, marmoset, orangutan, chimpanzee and the like, and the like.

Examples of the plasmid vector include plasmid vectors derived from Escherichia coli (e.g., pBR322, pBR325, pUC12, pUC13), plasmid vectors derived from Bacillus subtilis (e.g., pUB110, pTP5, pC194), plasmid vectors derived from yeast (e.g., pSH19, pSH15) and the like, which can be appropriately selected according to the kind of the host to be used and the object of use.

The kind of the virus vector can be appropriately selected according to the kind of the host to be used and object of use. For example, when an insect cell is used as a host, baculovirus vector and the like can be used. When a mammalian cell is used as a host, retrovirus vectors such as moloney murine leukemia virus vector, lentivirus vector, sindbis virus vector and the like, adenovirus vector, herpes virus vector, adeno-associated virus vector, parvovirus vector, vaccinia virus vector, sendai virus vector and the like can be used.

The promoter can be selected according to the kind of the host to be used, and one capable of initiating transcription in the host can be selected. For example, when the host is the genus Escherichia, trp promoter, lac promoter, T7 promoter and the like are preferable. When the host is the genus Bacillus, SPO1 promoter, SPO2 promoter, penP promoter and the like are preferable. When the host is yeast, PHO5 promoter, PGK promoter and the like are preferable. When the host is an insect cell, polyhedrin promoter, P10 promoter and the like are preferable. When the host is a mammalian cell, subgenomic (26S) promoter, CMV promoter, SRα promoter and the like are preferable.

The vector of the present invention may contain a signal sequence for antibody secretion. As the signal sequence for antibody secretion when it is produced in the periplasm of Escherichia coli, pelB signal sequence (Lei, S. P. et al J. Bacteriol. (1987) 169, 4379) may be used.

When desired, the vector of the present invention may contain enhancer, splicing signal, polyA addition signal, selection marker, SV40 replication origin (hereinafter sometimes to be abbreviated as SV40ori) and the like each in an operable manner. Examples of the selection marker include dihydrofolate reductase (hereinafter sometimes to be abbreviated as dhfr) gene [methotrexate (MTX) resistance], ampicillin resistance gene (sometimes to be abbreviated as $Amp^r$), neomycin resistance gene (sometimes to be abbreviated as $Neo^r$, G418 resistance) and the like.

By introducing the above-mentioned vector of the present invention into the above-mentioned host by gene transfer methods known per se (e.g., lipofection method, calcium phosphate method, microinjection method, proplast fusion method, electroporation method, DEAE dextran method, gene transfer method by Gene Gun etc.), a transformant with the vector introduced thereinto (transformant of the present invention) can be produced. When an expression vector is used as the vector to be introduced, the transformant can express the antibody of the present invention. The transformant of the present invention is useful for the production of the antibody of the present invention and the like.

The antibody of the present invention can be produced by culturing the transformant of the present invention by a method known per se according to the kind of the host, and isolating the antibody of the present invention from the culture. When the host is the genus *Escherichia*, the transformant is cultured in an appropriate medium such as LB medium, M9 medium and the like at generally about 15-43° C. for about 3-24 hr. When the host is the genus *Bacillus*, the transformant is cultured in an appropriate medium generally at about 30-40° C. for about 6-24 hr. When the host is yeast, the transformant is cultured in an appropriate medium such as Burkholder's medium and the like generally at about 20° C.-35° C. for about 24-72 hr. When the host is an insect cell or insect, the transformant is cultured in an appropriate medium such as Grace's Insect medium added with about 10% of bovine serum and the like generally at about 27° C. for about 3-5 days. When the host is an animal cell, the transformant is cultured in an appropriate medium such as MEM medium added with about 10% of bovine serum and the like generally at about 30° C.-40° C. for about 15-60 hr. In any culture, aeration and stirring may be performed as necessary.

As for the production method of antibody by genetic engineering, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137 and the like can be referred to.

The separation and purification of the antibody of the present invention from a culture is not limited in any manner, and the separation and purification methods generally used for purification of antibody can be employed. For example, antibody can be separated and purified by appropriately selecting and combining chromatography column, filter, ultrafiltration, salting out, solvent precipitation, solvent extraction, distillation, immunoprecipitation, SDS-polyacrylamide gel electrophoresis, isoelectric focusing, dialysis, recrystallization and the like.

Examples of the chromatography include affinity chromatography, ion exchange chromatography, hydrophobic chromatography, gel filtration, reversed-phase chromatography, adsorption chromatography and the like (Strategies for Protein Purification and Characterization: A Laboratory Course Manual. Ed Daniel R. Marshak et al., Cold Spring Harbor Laboratory Press, 1996). These chromatographys can be performed by using liquid phase chromatography, for example, liquid phase chromatography such as HPLC, FPLC and the like. Examples of the column to be used for affinity chromatography include protein A column and protein G column. For example, as a column using protein A, Hyper D, POROS, Sepharose FF (manufactured by GE Amersham Biosciences) and the like can be mentioned. The present invention also encompasses an antibody highly purified by these purification methods.

In addition, the present invention provides a pharmaceutical composition containing the above-mentioned antibody of the present invention as an active ingredient. The antibody and the pharmaceutical composition of the present invention are useful as drug delivery vehicles for delivering a drug to a cell or tissue expressing human membrane-anchored form ADAM28. A drug delivery vehicle means a carrier mediating delivery of a desired drug to a target cell or tissue. The cell or tissue expressing human membrane-anchored form ADAM28 is preferably cancer cell or cancer tissue. While the type of cancer is not particularly limited as long as it expresses human membrane-anchored form ADAM28, and liver cancer, colorectal cancer, renal cancer, melanoma, pancreatic cancer, thyroid cancer, gastric cancer, lung cancer (small cell lung cancer, non-small cell lung cancer), brain tumor, uterine cancer, breast cancer, multiple osteosarcoma, ovarian cancer, chronic leukemia, prostate cancer, acute lymphoblastic leukemia, germinoma, acute myeloid leukemia, malignant lymphoma, villous cancer, pediatric malignant tumor, gall bladder or bile duct cancer and the like can be mentioned. Whether the cell or tissue expresses human membrane-anchored form ADAM28 can be evaluated by flow cytometry, immunohistochemical staining, Western blotting using the antibody of the present invention, or an antibody that specifically recognizes human ADAM28, RT-PCR and the like.

When a desired drug is delivered to a cell or tissue expressing human membrane-anchored form ADAM28 by using the antibody of the present invention, an immune complex (immunoconjugate) containing the drug and the antibody of the present invention is administered to a human having a cell or tissue (e.g., cancer cell, cancer tissue) expressing human membrane-anchored form ADAM28. The kind of the drug to be conjugated with the antibody of the present invention is not particularly limited and, for example, a compound for injuring a cell or tissue (e.g., cancer cell or cancer tissue) expressing human membrane-anchored form ADAM28, thereby treating a disease caused by the cell or tissue (e.g., anti-cancer agent such as chemotherapeutic agent and the like, radioisotope, toxin); a labeling agent for detecting and imaging a cell or tissue expressing human membrane-anchored form ADAM28 (e.g., radioisotope, fluorescent substance, luminescence substance, enzyme) and the like can be mentioned. By administering an immune complex comprising a compound for injuring a cell or tissue (e.g., cancer cell or cancer tissue) expressing human membrane-anchored form ADAM28 to treat a disease caused by the cell or tissue and the antibody of the present invention to a human, the compound is selectively delivered to a cell or tissue (e.g., cancer cell or cancer tissue) expressing human membrane-anchored form ADAM28 in the human, the cell or tissue (e.g., cancer cell or cancer tissue) expressing human membrane-anchored form ADAM28 is injured in the human, and a disease caused by the cell or tissue (e.g., cancer) can be treated. Also, by administering an immune complex comprising a labeling agent for detecting and imaging a cell or tissue expressing human membrane-anchored form ADAM28 and the antibody of the present invention to a human, the labeling agent is selectively delivered to a cell or tissue (e.g., cancer cell or cancer tissue) expressing human membrane-anchored form ADAM28 in the human, and the cell or tissue expressing human membrane-anchored form ADAM28 can be specifically detected and imaged. The antibody of the present invention may be conjugated with polymer substances such as polyethylene glycol (PEG), hyaluronic acid and the like to improve stability in vivo.

A coupling scheme of the drug and the antibody of the present invention is not particularly limited as long as the immune complex is stably present in vivo, and the drug can be delivered to a cell or tissue expressing human membrane-anchored form ADAM28. For example, a direct conjugation of a drug to the antibody of the present invention, a conjugation of a drug to the antibody of the present invention via a spacer, a conjugation of a drug to the antibody of the present invention via an intermediate support (dextran, albumin etc.), a conjugation of a carrier such as a liposome encapsulating a drug, and the like to the antibody of the present invention and the like can be mentioned. A production method of such immune complex has already been established in the Technical Field (e.g., U.S. Pat. Nos. 5,057,313, 5,156,840).

Many of the cancer cells expressing human membrane-anchored form ADAM28 also express human secreted form ADAM28. Since conventionally-known anti-ADAM28 antibody (patent document 1) binds to the both, when this antibody is used in the missile therapy, secreted form ADAM28 may bind to the antibody in a competitive manner with membrane-anchored form ADAM28 to inhibit binding of the anti-ADAM28 antibody to cancer cells. In contrast, the antibody of the present invention has an activity to specifically bind to human membrane-anchored form ADAM28 and does not bind to human secreted form ADAM28, since an epitope of the antibody is in a region specific to human membrane-anchored form ADAM28. As a result, the present antibody binds to human membrane-anchored form ADAM28 without being inhibited by secreted form ADAM28, and can deliver a desired drug to a cell or tissue expressing human membrane-anchored form ADAM28. Therefore, the antibody of the present invention is superior as a drug delivery vehicle to a cell or tissue expressing human secreted form ADAM28 in addition to human membrane-anchored form ADAM28. Whether the cell or tissue expresses human secreted form ADAM28 can be evaluated by immunohistochemical staining, Western blotting using an antibody that specifically recognizes human secreted form ADAM28, RT-PCR and the like. It is known that the concentration of secreted form ADAM28 in the serum increases in some cancers along with the progression, metastasis, and recurrence of cancer and the like. It is advantageous to use the antibody of the present invention as a drug delivery vehicle in a human who had secreted form ADAM28 detected in the serum, or a human showing a higher concentration of secreted form ADAM28 in the serum than healthy individuals, as the subject of administration, since a desired drug can be delivered to a cell or tissue (e.g., cancer cell or cancer tissue) expressing human membrane-anchored form ADAM28 without being inhibited by secreted form ADAM28 in the blood flow.

The antibody and the aforementioned immune complex of the present invention can be formulated according to a conventional method (e.g., Remington's Pharmaceutical Science, latest edition, Mark Publishing Company, Easton, U.S.A.). Where necessary, moreover, it may contain a pharmaceutically acceptable carrier and/or additive. For example, it can contain surfactant (PEG, Tween etc.), excipient, antioxidant (ascorbic acid etc.), colorant, flavor, preservative, stabilizer, buffering agent (phosphate, citrate, other organic acid etc.), chelating agent (EDTA etc.), suspending agent, isotonizing agent, binder, disintegrant, lubricant, glidant, corrigent and the like. Not being limited to these, the pharmaceutical composition of the present invention may contain other conventional carriers as appropriate. Specific examples include light anhydrous silicic acid, lactose, crystalline cellulose, mannitol, starch, carmellose calcium, carmellose sodium, hydroxypropylcellulose, hydroxypropylmethylcellulose, polyvinyl acetaldiethylaminoacetate, polyvinylpyrrolidone, gelatin, medium-chain fatty acid triglyceride, polyoxyethylene hydrogenated castor oil 60, sucrose, carboxymethylcellulose, cornstarch, inorganic salts and the like. It may also contain other low-molecular-weight polypeptide, proteins such as serum albumin, gelatin and immunoglobulin and the like, as well as amino acid. When an aqueous solution for injection is formulated, the antibody of the present invention or the aforementioned immune complex is dissolved in, for example, isotonic solution containing saline, glucose or other auxiliary agent. Examples of the auxiliary agent include D-sorbitol, D-mannose, D-mannitol, and sodium chloride, and may be used in combination with suitable solubilizing agents, for example, alcohol (ethanol etc.), polyalcohol (propylene glycol, PEG etc.), non-ionic surfactant (polysorbate80, HCO-50) and the like.

Where necessary, polypeptide may also be encapsulated in a microcapsule (microcapsules made of hydroxymethylcellulose, gelatin, poly[methylmethacrylate] and the like), or formulated as a colloid drug delivery system (liposome, albumin microsphere, microemulsion, nanoparticles and nanocapsule etc.) (see Remington's Pharmaceutical Science 16th edition &, Oslo Ed. (1980) etc.). Furthermore, a method of formulating a drug as a sustained-release medicament is also known, and applicable to polypeptide (Langer et al., J. Biomed. Mater. Res. (1981)15: 167-277; Langer, Chem. Tech. (1982)12: 98-105; U.S. Pat. No. 3,773,919; EP-A-58, 481; Sidman et al., Biopolymers (1983) 22: 547-56; EP No. 133,988). Furthermore, it is also possible to increase the liquid amount to be subcutaneously administered by adding or blending hyaluronidase to or with the present agent (e.g., WO 2004/078140 etc.).

The content of the antibody of the present invention or the aforementioned immune complex in a pharmaceutical composition is, for example, about 0.01-100 wt %, preferably 0.1-99.9%, of the whole pharmaceutical composition.

While the pharmaceutical composition of the present invention can be administered both orally and parenterally, it is preferably administered parenterally. Specifically, it is administered to patients by injection or transdermal administration. As an example of the dosage form of injection, it can be administered systemically or topically by intravenously injection, intramuscular injection, subcutaneous injection and the like. It may also be administered to the treatment site or in the vicinity thereof by topical injection, particularly intramuscular injection. Examples of the dosage form of transdermal administration include ointment, gel, cream, plaster, patch and the like, which can be administered systemically or topically. In addition, the administration method can be appropriately selected according to the age and symptom of the patients. The dose can be selected from, for example, the range of 0.5 mg-10 mg/kg body weight as the antibody or immune complex of the present invention. However, the pharmaceutical composition of the present invention is not limited by these doses.

All references cited in the present specification, including publication, patent document and the like, are hereby incorporated individually and specifically by reference, to the extent that the entireties thereof have been specifically disclosed herein.

EXAMPLES

The present invention is explained in more detail in the following by referring to Examples, which are not to be construed as limitative. Various gene manipulations in the Examples followed the method described in Molecular cloning third. ed. (Cold Spring Harbor Lab. Press, 2001).

Example 1

Preparation of Antibody that Specifically Recognizes Human Membrane-Anchored Form ADAM28

A mouse was immunized with a fusion protein in which a membrane-anchored form-specific region of human ADAM28 (region of the 524th-659th amino acids in the amino acid sequence shown in SEQ ID NO: 2) is fused to C-terminal of MBP, hybridoma was established by the iliac lymph node method, and clone 2B6D10 that reacts with only human membrane-anchored form ADAM28 was selected by flow cytometry.

(1) ELISA

The fusion protein, the immunogen, was used as an antigen, the culture supernatant of 2B6D10 was used as the primary antibody, and an anti-mouse IgG-HRP antibody (1:100000) was used as the secondary antibody. The results are shown in the following Table.

TABLE 1

| antigen | OD450 |
|---|---|
| MBP-human ADAM28m 524-659 | 2.390 |
| MBP | 0.023 |

(2) Tissue Staining

CHO-K1 cells co-transfected with human membrane-anchored form ADAM28 and EGFP were treated with a 2B6D10 antibody (5 µg/ml) at 4° C. for 1.5 hr. The cells were washed, and treated with anti-mouse IgG-Alexa555 (1:300) at 4° C. for 1 hr. The cells were washed, incubated at 37° C. for 0 min or 90 min, fixed and observed. The results are shown in FIG. 1.

Figure 2:
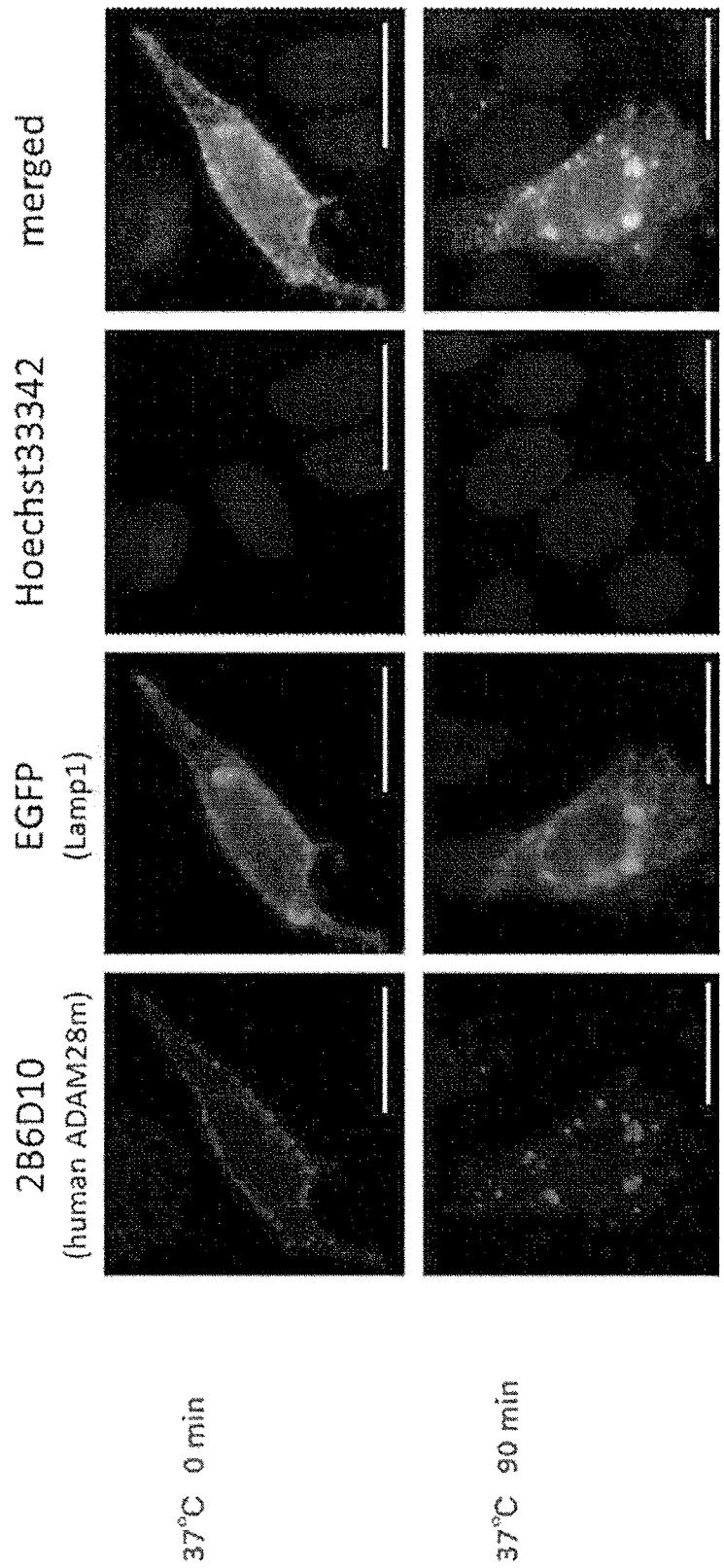
FIG. 2 shows a 2B6D10 antibody-stained image of CHO-K1 cells, transfected with human membrane-anchored form ADAM28.

The 2B6D10 antibody bound to CHO-K1 cells transfected with human membrane-anchored form ADAM28. After antibody staining, the cells were incubated at 37° C., as a result of which internalization of antibody was observed. The intracellular localization was identical with a lysosome marker Lamp1-EGFP (FIG. 2).

(3) Cross-Reactivity to Mouse ADAM28

Figure 3:
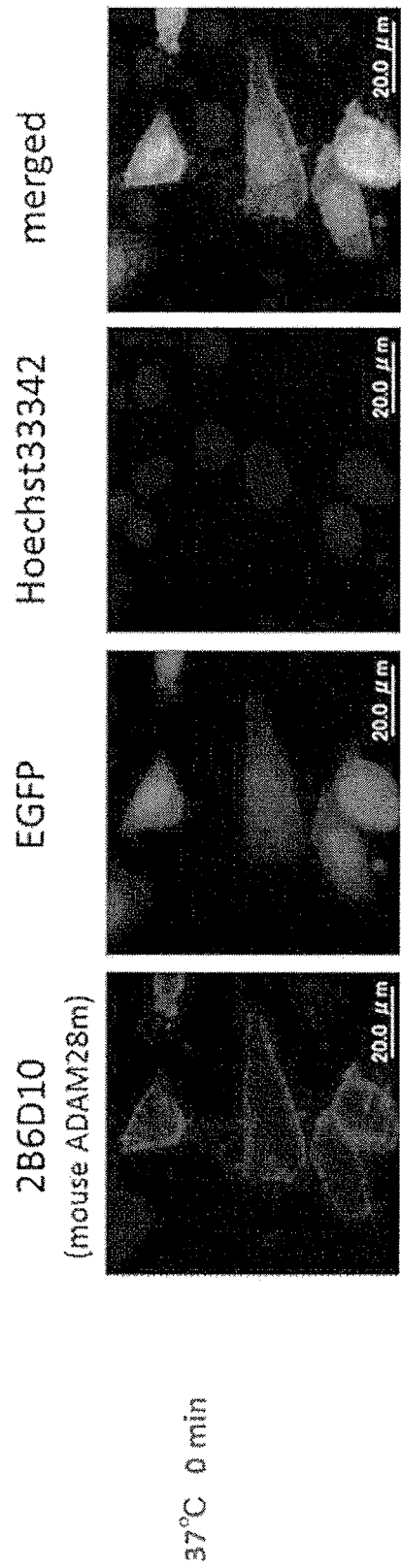
FIG. 3 shows a 2B6D10 antibody-stained image of CHO-K1 cells, transfected with mouse membrane-anchored form ADAM28.

CHO-K1 cells co-transfected with mouse membrane-anchored form ADAM28 and EGFP were treated with 2B6D10 antibody (5 µg/ml) at 4° C. for 1.5 hr. The cells were washed and treated with anti-mouse IgG-Alexa555 (1:300) at 4° C. for 1 hr. The cells were washed, fixed and observed. The results are shown in, FIG. 3.

The 2B6D10 antibody cross-reacted with mouse membrane-anchored form ADAM28.

(4) Sequence Analysis of Variable Region

Total RNA was extracted from the hybridoma of 2B6D10, cDNA of the light chain and heavy chain variable region of the antibody was amplified by RT-PCR, and cDNA sequence was analyzed. The amino acid sequence of the light chain and heavy chain variable region of the 2B6D10 antibody was deduced from the cDNA sequence. The results are shown in the following Table.

TABLE 2

| VL | | |
|---|---|---|
| Region | Sequence Fragment | Length |
| LFR1 | DVLMTQTPLSLPVSLGDQASISC (SEQ ID NO: 13) | 23 |
| CDR-L1 | RSSQNIIHSDGNTYLE (SEQ ID NO: 5) | 16 |
| LFR2 | WYLQKPGQSPKFLIY (SEQ ID NO: 14) | 15 |
| CDR-L2 | KVSNRFS (SEQ ID NO: 6) | 7 |
| LFR3 | GVPDRFSGSGSGTDFTLKISRVEAEDLGVYYC (SEQ ID NO: 15) | 32 |

TABLE 2-continued

| VL | | |
|---|---|---|
| Region | Sequence Fragment | Length |
| CDR-L3 | LQGSHVPWT (SEQ ID NO: 7) | 9 |
| LFR4 | FGGGTKLEIKRA (SEQ ID NO: 16) | 12 |

TABLE 3

| VH | | |
|---|---|---|
| Region | Sequence Fragment | Length |
| HFR1 | QVQLQQSGAELARPGASVKLSCKASGYTFT (SEQ ID NO: 17) | 30 |
| CDR-H1 | SYGIS (SEQ ID NO: 8) | 5 |
| HFR2 | WVKQRTGQGLEWIG (SEQ ID NO: 18) | 14 |
| CDR-H2 | EIYPRSGNTYYNEKFKG (SEQ ID NO: 9) | 17 |
| HFR3 | KATLTADKSSSTAYMELRRLTSEDSAVFFCAR (SEQ ID NO: 19) | 32 |
| CDR-H3 | ENVYSSNYGFAF (SEQ ID NO: 10) | 12 |
| HFR4 | WGQGTLVTVSA (SEQ ID NO: 20) | 11 |

The full-length amino acid sequences of the light chain and heavy chain variable regions of the 2B6D10 antibody are shown in SEQ ID NOs: 11 and 12, respectively.

TABLE 4

2B6D10 light chain variable region:
DVLMTQTPLSLPVSLGDQASISCRSSQNIIHSDGNTYLEWYLQKPGQSP
KFLIYKVSNRFSGVPDRFSGSGSGTDFTLKISRVEAEDLGVYYCLQGSH
VPWTFGGGTKLEIKRA (SEQ ID NO: 11)

2B6D10 heavy chain variable region:
QVQLQQSGAELARPGASVKLSCKASGYTFTSYGISWVKQRTGQGLEWIG
EIYPRSGNTYYNEKFKGKATLTADKSSSTAYMELRRLTSEDSAVFFCAR
ENVYSSNYGFAFWGQGTLVTVSA (SEQ ID NO: 12)

Example 2

Fusion proteins comprising a partial sequence of the following regions of human membrane-anchored form ADAM28s (SEQ ID NO: 2) added to the C-terminal of MBP were respectively prepared. 524-562, 554-596, 588-630, 622-659, 524-543, 534-553, 544-562, 536-545, 538-547, 540-549, 542-551, 536-543, 537-544, 538-545 (each value shows amino acid number in the amino acid sequence shown in SEQ ID NO: 2)

The reactivity of anti-human membrane-anchored form ADAM28 antibody 2B6D10 with the above-mentioned fusion proteins was evaluated by Western blotting. As a result, 2B6D10 strongly bound to fusion proteins containing a partial sequence of the regions 536-543 (524-562, 524-543, 534-553, 536-545, and 536-543). The results suggest that the epitope of 2B6D10 is contained in the 536-543 region (EGGSKYGY, SEQ ID NO: 27) of human membrane-anchored form ADAM28 (SEQ ID NO: 2).

Example 3

Comparison of Reactivity of 2B6D10 Antibody with Human Membrane-Anchored form ADAM28 and Those with Mouse Membrane-Anchored Form ADAM28 by ELISA A fusion protein in which a 524-659 region of human membrane-anchored form ADAM28 (SEQ ID NO: 2) is added to C-terminal of MBP (MBP-human ADAM28m 524-659) and a fusion protein in which a 527-622 region of mouse membrane-anchored form ADAM28 (SEQ ID NO: 26) (corresponding to 524-659 region of human membrane-anchored form ADAM28) is added to C-terminal of MBP (MBP-mouse ADAM28m 527-622) were prepared and used for ELISA. Each antigen was immobilized on ELISA plate at 5 μg/ml, and reacted with 2B6D10 antibody diluted for the measurement. Thereafter, samples were reacted with the secondary antibody, 1:10000-diluted anti-mouse IgG-HRP (Jackson ImmunoResearch Laboratories). Detection was performed by color development with TMB.

The results are shown in FIG. 4. The results have clarified that 2B6D10 antibody has equivalent reactivity with human membrane-anchored form ADAM28 and mouse membrane-anchored form ADAM28.

Example 4

Protein Interaction Analysis by Surface Plasmon Resonance (SPR)

A fusion protein in which a 524-659 region of human membrane-anchored form ADAM28 (SEQ ID NO: 2) is added to C-terminal of MBP (MBP-human ADAM28m 524-659) and a fusion protein in which a 527-622 region of mouse membrane-anchored form ADAM28 (SEQ ID NO: 26) is added to C-terminal of MBP (MBP-mouse ADAM28m 527-622) were each immobilized on CM5 sensor chip (GE Healthcare Life Sciences, Buckinghamshire, UK) by amine-coupling and 2B6D10 antibody was injected to a flow cell by using BIAcore 3000 (GE Healthcare Life Sciences). The $K_D$ value was calculated from the measured Ka and Kd values.

The results are shown in the following Table.

TABLE 5

| analyte | ligand | KD value |
|---------|--------|----------|
| 2B6D10 | MBP-human ADAM28m 524-659 | 9.35E-11 (M) |
| 2B6D10 | MBP-mouse ADAM28m 527-622 | 2.36E-10 (M) |

As a result, the KD values of 2B6D10 antibody against human membrane-anchored form ADAM28 and mouse membrane-anchored form ADAM28 were $9.35 \times 10^{-11}$ M and $2.36 \times 10^{-10}$ M, respectively, thus showing equivalent high affinity for the both.

INDUSTRIAL APPLICABILITY

According to the present invention, an anti-human ADAM28 antibody which specifically binds to human membrane-anchored form ADAM28, and is useful for the missile therapy of cancer cells expressing membrane-anchored form ADAM28 is provided.

The contents disclosed in any publication cited herein, including patents and patent applications, are hereby incorporated in their entireties by reference, to the extent that they have been disclosed herein.

This application is based on a patent application No. 2015-045244 filed in Japan (filing date: Mar. 6, 2015), the contents of which are incorporated in full herein.

The invention claimed is:

1. An antibody comprising a light chain variable region and a heavy chain variable region,
    wherein the antibody has an activity to specifically bind to human membrane-anchored form ADAM28,
    wherein the antibody binding site on human membrane-anchored form ADAM28 is located in a region consisting of the 524th-659th amino acids in the amino acid sequence shown in SEQ ID NO: 2,
    wherein the light chain variable region comprises CDR1 comprising the amino acid sequence shown in SEQ ID NO: 5, CDR2 comprising the amino acid sequence shown in SEQ ID NO: 6, and CDR3 comprising the amino acid sequence shown in SEQ ID NO: 7, and
    wherein the heavy chain variable region comprises CDR1 comprising the amino acid sequence shown in SEQ ID NO: 8, CDR2 comprising the amino acid sequence shown in SEQ ID NO: 9, and CDR3 comprising the amino acid sequence shown in SEQ ID NO: 10.

2. The antibody according to claim 1, wherein the antibody binding site on human membrane-anchored form ADAM28 is located in a region of the 536th-543rd amino acids in the amino acid sequence shown in SEQ ID NO: 2.

3. The antibody according to claim 1, which does not have an activity to bind to human secreted form ADAM28.

4. The antibody according to claim 1, wherein the light chain variable region comprises the amino acid sequence shown in SEQ ID NO: 11, and the heavy chain variable region comprises the amino acid sequence shown in SEQ ID NO: 12.

5. A pharmaceutical composition comprising the antibody according to claim 1.

6. A drug delivery vehicle for delivering a drug to a cell or tissue that expresses a human membrane-anchored form ADAM28, comprising the antibody according to claim 1.

7. The drug delivery vehicle according to claim 6, wherein the cell or tissue further expresses human secreted form ADAM28.

8. The drug delivery vehicle according to claim 6, wherein the cell or tissue is a cancer cell or cancer tissue.

9. A method of delivering a drug to a cell or tissue expressing human membrane-anchored form ADAM28 in human, comprising administering an immune complex comprising the drug and the antibody according to claim 1 to a human.

10. A polynucleotide encoding the antibody according to claim 1.

11. A vector comprising the polynucleotide according to claim 10.

12. A transformant comprising the vector according to claim 11.

13. The method according to claim 9, wherein the cell or tissue further expresses human secreted form ADAM28.

14. The method according to claim 9, wherein the cell or tissue is a cancer cell or cancer tissue.

* * * * *